US012662485B2

(12) United States Patent
Browning et al.

(10) Patent No.: US 12,662,485 B2
(45) Date of Patent: Jun. 23, 2026

(54) SUBSTITUTED PYRAZOLO[4,3-D]PYRIMIDINES AS GUT-TARGETED PHOSPHODIESTERASE INHIBITORS

(71) Applicant: AUGUSTA UNIVERSITY RESEARCH INSTITUTE, INC., Augusta, GA (US)

(72) Inventors: Darren Browning, Evans, GA (US); Iryna Lebedyeva, Augusta, GA (US)

(73) Assignee: AUGUSTA UNIVERSITY RESEARCH INSTITUTE, INC., Augusta, GA (US)

( * ) Notice: Subject to any disclaimer, the term of this patent is extended or adjusted under 35 U.S.C. 154(b) by 666 days.

(21) Appl. No.: 17/999,101

(22) PCT Filed: May 20, 2021

(86) PCT No.: PCT/US2021/033334
§ 371 (c)(1),
(2) Date: Nov. 17, 2022

(87) PCT Pub. No.: WO2021/236891
PCT Pub. Date: Nov. 25, 2021

(65) Prior Publication Data

US 2023/0348470 A1 Nov. 2, 2023

Related U.S. Application Data

(60) Provisional application No. 63/027,649, filed on May 20, 2020.

(51) Int. Cl.
*C07D 487/04* (2006.01)
*C07D 519/00* (2006.01)

(52) U.S. Cl.
CPC ......... *C07D 487/04* (2013.01); *C07D 519/00* (2013.01)

(58) Field of Classification Search
CPC .................................................... C07D 487/04
USPC .......................................................... 544/262
See application file for complete search history.

(56) References Cited

U.S. PATENT DOCUMENTS

| | | | | |
|---|---|---|---|---|
| 5,719,283 | A * | 2/1998 | Bell | C07D 487/04 544/118 |
| 2005/0069276 | A1 | 3/2005 | Alken | |
| 2009/0264413 | A1 | 10/2009 | Lee et al. | |
| 2014/0179701 | A1 | 6/2014 | Lee et al. | |
| 2017/0027942 | A1 | 2/2017 | Fossel | |

OTHER PUBLICATIONS

International Search Report issued in PCT/US2021/033334 on Oct. 1, 2021 (4 pages).
Written Opinion issued in PCT/US2021/033334 on Oct. 1, 2021 (5 pages).
Islam et al., "Sildenafil Suppresses Inflammation-Driven Colorectal Cancer in Mice", Cancer Prev Res (Phila). Jul. 2017;10(7):377-388. doi: 10.1158/1940-6207.CAPR-17-0015. Epub May 3, 2017.

* cited by examiner

*Primary Examiner* — Douglas M Willis
(74) *Attorney, Agent, or Firm* — Pabst Patent Group LLP

(57) ABSTRACT

Provided herein are compounds that inhibit phosphodiesterase 5 (PDE5) and methods of use thereof. In some forms, the compounds can have a structure according to Formula I:

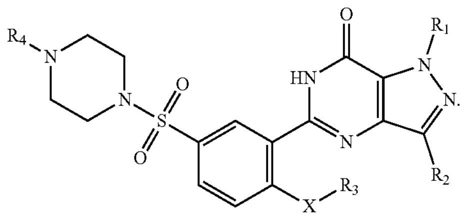

Also provided are pharmaceutical compositions and medicaments that include the compounds described herein as well as methods of treating gastrointestinal diseases and disorders such as intestinal cancers, chronic constipation, and inflammatory bowel disease.

8 Claims, 9 Drawing Sheets

SUBSTITUTED PYRAZOLO[4,3-D]PYRIMIDINES AS GUT-TARGETED PHOSPHODIESTERASE INHIBITORS

CROSS REFERENCE TO RELATED APPLICATIONS

This application is a national stage application, filed under 35 U.S.C. § 371, of International Patent Application No. PCT/US2021/033334, filed on May 20, 2021, which claims benefit of and priority to U.S. Provisional Application No. 63/027,649, filed on May 20, 2020, each of which are incorporated herein by reference in their entirety.

STATEMENT REGARDING FEDERALLY SPONSORED RESEARCH OR DEVELOPMENT

This invention was made with government support under CA172627 awarded by the National Institutes of Health. The government has certain rights in the invention.

FIELD OF THE INVENTION

Aspects of the invention are generally directed to small molecule inhibitors of phosphodiesterase 5 (PDE5) and methods of use thereof.

BACKGROUND OF THE INVENTION

Chronic constipation (CC) is one of the most common gastrointestinal complaints affecting at least 20% of Americans. While not a life-threatening condition, chronic constipation can have a profound negative effect on quality of life and is responsible for over 2.5 million physician visits and 100,000 hospitalizations annually in the United States. Treatments for CC have varying degrees of efficacy, most with unsatisfactory results and significant side effects. A new class of agents called GC-C agonists became available in recent years that function by stimulating the production of a chemical called cGMP in the gut lining. The GC-C agonist drugs have been highly effective for a cohort of CC patients, creating a total revenue of $325 million for sales of LINZESS and $55 million for sales of TRULANCE in the United States in 2019. The success of the GC-C agonists for CC demonstrates the large unmet clinical need, and the utility of cGMP-elevation as a therapeutic approach.

However, GC-C agonists are not without side effects and limitations. Diarrhea is a significant side effect. The drugs are also not approved for use in children under the age of 16.

Cancer of the colorectum (CRC) is one of the most common in the world, representing 8% of all cancer diagnoses and all cancer deaths. According to the National Cancer Institute, the average risk of developing CRC in our lifetime is around 1 in 23 in the United States, where approximately 150,000 cases are diagnosed annually. First-person relatives of cancer patients and people with prior polypectomy are up to 5 times more likely to develop CRC than the general population, and reducing their risk is a high priority.

According to the American Gastroenterological Association, around $40 billion is spent annually for colonoscopy screening for CRC prevention, but this procedure has numerous economic, cultural, and geographical limitations. Chemoprevention is therefore a priority for people at high risk for CRC, but there are no drugs currently approved for this unmet clinical need. Extensive preclinical work and two recent large-cohort retrospective epidemiological studies underscore the utility of repurposing PDE5i for CRC prevention.

GI diseases, including CC and CRC, affect millions of men and women in the United States and are a massive health burden throughout the world. Available drugs to treat many of the diseases are inadequate and have side-effects that prevent their long-term use. There is currently nothing available for the primary chemoprevention of CRC. Accordingly, there remains a strong unmet need for new PDE5 inhibiting compounds with improved efficacy for treating and/or preventing gastrointestinal diseases and disorders such as intestinal cancers and inflammatory bowel disease.

Therefore, it is an object of the invention to provide PDE5 specific inhibitors, for example, small molecule PDE5 inhibitors.

It is still another object of the invention to provide pharmaceutical compositions containing small molecule PDE5 inhibitors that specifically inhibit PDE5.

It is still another object to provide methods of treating gastrointestinal diseases and disorders with reduced undesirable or harmful side effects.

SUMMARY OF THE INVENTION

Phosphodiesterase 5 (PDE5) small molecule inhibitor compositions and methods of their use are provided.

One embodiment provides a compound of Formula I:

Formula I

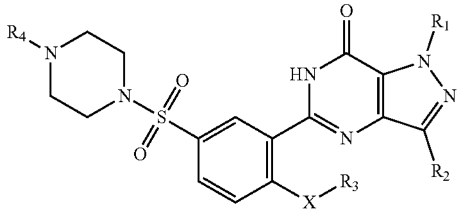

wherein $R_1$ and $R_2$ are each independently unsubstituted or substituted halogen, $C_{1-10}$ alkyl, $C_{1-10}$ alkoxy, $C_{3-10}$ cycloalkyl, aryl, and heteroaryl;

X is each independently —$CH_2$, —O, —S or —NH;

$R_3$ is independently unsubstituted or substituted OH, CN, COOH, $NO_2$, $NH_2$, $CONH_2$, $CH_2NH_2$, halogen, $C_{1-10}$ alkyl, $C_{1-10}$ alkoxy, $C_{3-10}$ cycloalkyl, aryl, and heteroaryl;

$R_4$ is independently unsubstituted or substituted H, OH, halogen, $C_{1-10}$ alkyl, $C_{1-10}$ alkoxy, $C_{3-10}$ cycloalkyl, aryl, heteroaryl, NCO, —$CH_2$-halogen, —CHO, —CN, $NO_2$, $NH_2$, —$CO(CH_2)_nNH_2$, —$CO(CH_2)_nNHR_6$, —$CO(CH_2)_nNR_6R_7$, —$COR_8$, —$COCHOHR_9$, —COOH, —$CH_2COOH$, —$COCH_2COOH$, —$CO$-$COR_{10}$, —$SO_2R_{11}$;

$R_6$ and $R_7$ are each independently H or unsubstituted or substituted $C_{1-10}$ alkyl;

$R_8$, $R_9$ and $R_{10}$ are each independently unsubstituted or substituted $C_{1-10}$ alkyl;

$R_{11}$ is independently OH, ONa or $C_{1-10}$ alkyl, $NH_2$; and n is 1, 2, 3, 4, 5 or 6;

or a hydrate, enantiomer, tautomer, stereoisomers, solvate, zwitterion, polymorph, prodrug, or a pharmaceutically acceptable salt thereof.

Other embodiment provides a compound of Formula II:

Formula II

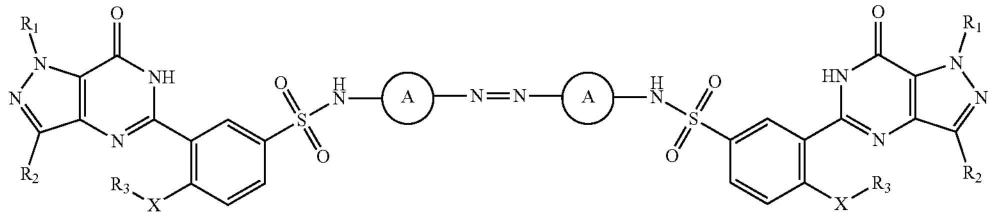

wherein $R_1$ and $R_2$ are each independently unsubstituted or substituted halogen, $C_{1-10}$ alkyl, $C_{1-10}$ alkoxy, $C_{3-10}$ cycloalkyl, aryl, and heteroaryl;

X is each independently —$CH_2$, —O, —S or —NH;

$R_3$ is independently unsubstituted or substituted OH, CN, COOH, $NO_2$, $NH_2$, $CONH_2$, $CH_2NH_2$, halogen, $C_{1-10}$ alkyl, $C_{1-10}$ alkoxy, $C_{3-10}$ cycloalkyl, aryl, and heteroaryl; and ring A is aryl, cycloalkyl or heteroaryl ring;

or a hydrate, enantiomer, tautomer, stereoisomers, solvate, zwitterion, polymorph, prodrug, or a pharmaceutically acceptable salt thereof.

Another embodiment provides a compound of Formula III:

Formula III

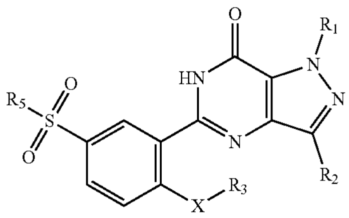

wherein $R_1$ and $R_2$ are each independently unsubstituted or substituted halogen, $C_{1-10}$ alkyl, $C_{1-10}$ alkoxy, $C_{3-10}$ cycloalkyl, aryl, and heteroaryl;

X is each independently —$CH_2$, —O, —S or —NH;

$R_3$ is independently unsubstituted or substituted OH, CN, COOH, $NO_2$, $NH_2$, $CONH_2$, $CH_2NH_2$, halogen, $C_{1-10}$ alkyl, $C_{1-10}$ alkoxy, $C_{3-10}$ cycloalkyl, aryl, and heteroaryl; and $R_5$ is independently unsubstituted or substituted H, OH, halogen, $C_{1-10}$ alkyl, $C_{1-10}$ alkoxy, $C_{3-10}$ cycloalkyl, aryl, heteroaryl, NCO, —$CH_2$-halogen, —CHO, —CN, —$NO_2$, —$NH_2$, —NH—, —NH—$C_{1-10}$ alkyl, —NH—$C_{1-10}$ alkoxy, —NH—$C_{3-10}$ cycloalkyl, —NH-aryl, —NH-heteroaryl, —COOH, —$CH_2COOH$, optionally mono-, di- or poly-substituted with —$B(OH)_2$, —CHO, —COOH, —$CH_2COOH$, —OH, —CN, —$SO_3H$, —$SO_3Na$, —$SO_2NH_2$, —$CH_3CO$, $NO_2$, $NH_2$, $CONH_2$, $CH_2NH_2$, halogen, $C_{1-10}$ alkyl, $C_{1-10}$ alkoxy, $C_{3-10}$ cycloalkyl, aryl, and heteroaryl, further optionally substituted with —COOH or —$SO_3H$;

or a hydrate, enantiomer, tautomer, stereoisomers, solvate, zwitterion, polymorph, prodrug, or a pharmaceutically acceptable salt thereof.

In other aspect, various embodiments provide a process for preparing a compound of Formula I, II or III or a pharmaceutically acceptable salt thereof.

Another embodiment provides a pharmaceutical composition containing a compound of Formula I, II or III or a pharmaceutically acceptable salt thereof, and optionally a pharmaceutically acceptable carrier, adjuvant or vehicle.

Another embodiment provides a method of inhibiting PDE5 in a subject in need thereof, including the step of contacting the subject's cells expressing PDE5 with a compound of Formula I, II or III or a pharmaceutical composition thereof.

Other embodiment provides a method of treating a PDE5-related disease, disorder or condition in a subject in need thereof by administering to the subject a therapeutically effective amount of the compound of Formula I, II or III or a pharmaceutical composition thereof.

Another embodiment provides a method of treating an intestinal or bowel disorder in a subject in need thereof by administering to the subject a therapeutically effective amount of the compound of Formula I, II or III or a pharmaceutical composition thereof that increases cellular level of cGMP in the intestinal mucosa or increases the activity of a PKG in the intestinal mucosa to reduce one or more symptoms of the intestinal bowel disorder.

Other embodiment provides a method of normalizing intestinal motility and transit in a subject in need thereof by administering to the subject a therapeutically effective amount of the compound of Formula I, II or III or a pharmaceutical composition thereof that increases cellular level of cGMP in the intestinal to normalize intestinal motility.

Another embodiment provides a method of treating intestinal permeability in a subject in need thereof by administering to the subject a therapeutically effective amount of the compound of Formula I, II or III or a pharmaceutical composition thereof that increases cellular level of cGMP in the intestinal mucosa or increases the activity of a PKG in the intestinal mucosa to repair the intestinal epithelial barrier.

Another embodiment provides a method of preventing or slowing the development of colorectal cancer in a subject in need thereof by administering to the subject a therapeutically effective amount of the compound of Formula I, II or III or a pharmaceutical composition thereof that increases cellular level of cGMP in the intestinal mucosa to reduce intestinal neoplasia.

DETAILED DESCRIPTION OF THE INVENTION

I. Definitions

Figure 1A:
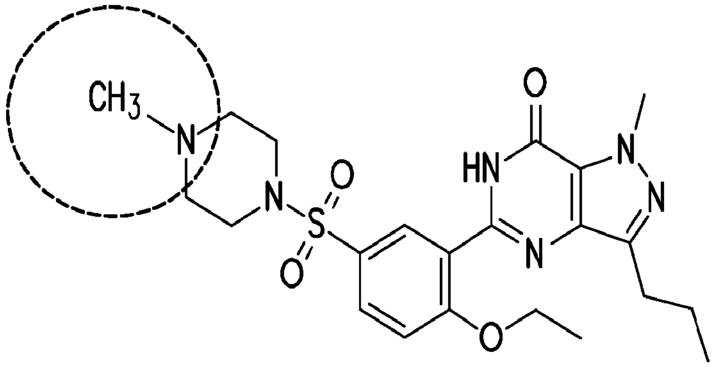
FIG. 1A is the chemical structure of the parent compound sildenafil and FIG. 1B is the chemical structure of the carboxylic acid containing analog malonyl-sildenafil. The chemical change is circled.

The following terms are intended to have the meanings presented therewith below and are useful in understanding the description and intended scope of the present invention.

When describing the invention, which may include compounds, pharmaceutical compositions containing such compounds and methods of using such compounds and compositions, the following terms, if present, have the following meanings unless otherwise indicated. It should also be understood that when described herein any of the moieties defined forth below may be substituted with a variety of substituents, and that the respective definitions are intended to include such substituted moieties within their scope as set out below. Unless otherwise stated, the term 'substituted' is to be defined as set out below. It should be further understood that the terms "groups" and "radicals" can be considered interchangeable when used herein.

The articles "a" and "an" may be used herein to refer to one or to more than one (i.e., at least one) of the grammatical objects of the article. By way of example "an analogue" means one analogue or more than one analogue.

As used herein, the term "pharmaceutical composition" means a mixture comprising a pharmaceutically acceptable active ingredient, in combination with suitable pharmaceutically acceptable excipients. In one embodiment the pharmaceutically acceptable ingredient is a pharmaceutically acceptable acid addition salt of the compound of formula I, II or III, or a solvate or hydrate of this acid addition salt.

Pharmaceutical excipients are substances other than the pharmaceutically acceptable active ingredient which have been appropriately evaluated for safety and which are intentionally included in an oral solid dosage form. For example, excipients can aid in the processing of the drug delivery system during its manufacture, protect, support or enhance stability, bioavailability or patient acceptability, assist in product identification, or enhance any other attribute of the overall safety, effectiveness or delivery of the drug during storage or use. Examples of excipients include, for example but without limitation inert solid diluents (bulking agent e.g., lactose), binders (e.g., starch), glidants (e.g., colloidal silica), lubricants (e.g., non-ionic lubricants such as vegetable oils), disintegrants (e.g., starch, polivinylpyrrolidone), coating better polymers (e.g., hydroxypropyl methylcellulose), colorants (e.g., iron oxide), and/or surfactants (e.g., non-ionic surfactants).

As used herein, the term "pharmaceutical formulation" means a composition in which different chemical substances, including the active drug, are combined to produce a final medicinal product. Examples of formulation include enteral formulations (tablets, capsules), parenteral formulations (liquids, lyophilized powders), or topical formulations (cutaneous, inhalable).

"Pharmaceutically acceptable" means approved or approvable by a regulatory agency of the Federal or a state government or the corresponding agency in countries other than the United States, or that is listed in the U.S. Pharmacopoeia or other generally recognized pharmacopoeia for use in animals, and more particularly, in humans.

"Pharmaceutically acceptable salt" refers to a salt of a compound of formula I, II or III or derivatives thereof that is pharmaceutically acceptable and that possesses the desired pharmacological activity of the parent compound. In particular, such salts are non-toxic may be inorganic or organic acid addition salts and base addition salts. Specifically, such salts include: (1) acid addition salts, formed with inorganic acids such as hydrochloric acid, hydrobromic acid, sulfuric acid, nitric acid, phosphoric acid, and the like; or formed with organic acids such as acetic acid, propionic acid, hexanoic acid, cyclopentanepropionic acid, glycolic acid, pyruvic acid, lactic acid, malonic acid, succinic acid, malic acid, maleic acid, fumaric acid, tartaric acid, citric acid, benzoic acid, 3-(4-hydroxybenzoyl) benzoic acid, cinnamic acid, mandelic acid, methanesulfonic acid, ethanesulfonic acid, 1,2-ethane-disulfonic acid, 2-hydroxyethanesulfonic acid, benzenesulfonic acid, 4-chlorobenzenesulfonic acid, 2-naphthalenesulfonic acid, 4-toluenesulfonic acid, camphorsulfonic acid, 4-methylbicyclo[2.2.2]-oct-2-ene-1-carboxylic acid, glucoheptonic acid, 3-phenylpropionic acid, trimethylacetic acid, tertiary butylacetic acid, lauryl sulfuric acid, gluconic acid, glutamic acid, hydroxynaphthoic acid, salicylic acid, stearic acid, muconic acid, and the like; or (2) salts formed when an acidic proton present in the parent compound either is replaced by a metal ion, e.g. an alkali metal ion, an alkaline earth ion, or an aluminum ion; or coordinates with an organic base such as ethanolamine, diethanolamine, triethanolamine, N-methylglucamine and the like. Salts further include, by way of example only, sodium, potassium, calcium, magnesium, ammonium, tetraalkylammonium, and the like; and when the compound contains a basic functionality, salts of non-toxic organic or inorganic acids, such as hydrochloride, hydrobromide, tartrate, mesylate, acetate, maleate, oxalate and the like. More particularly, such salts are formed with hydrobromic acid, hydrochloric acid, sulfuric acid, toluenesulfonic acid, benzenesulfonic acid, oxalic acid, maleic acid, naphthalene-2-sulfonic acid, naphthalene-1,5-disulfonic acid, 1-2-ethane disulfonic acid, methanesulfonic acid, 2-hydroxy ethanesulfonic acid, phosphoric acid, ethane sulfonic acid, malonic acid, 2-5-dihydroxybenzoic acid, or L-Tartaric acid.

The term “pharmaceutically acceptable cation” refers to an acceptable cationic counter-ion of an acidic functional group. Such cations are exemplified by sodium, potassium, calcium, magnesium, ammonium, tetraalkylammonium cations, and the like.

“Pharmaceutically acceptable vehicle” refers to a diluent, adjuvant, excipient or carrier with which a compound of the invention is administered.

“Solvate” refers to forms of the compound that are associated with a solvent, usually by a solvolysis reaction. This physical association includes hydrogen bonding. Conventional solvents include water, ethanol, acetic acid and the like. The compounds of the invention may be prepared e.g. in crystalline form and may be solvated or hydrated. Suitable solvates include pharmaceutically acceptable solvates, such as hydrates, and further include both stoichiometric solvates and non-stoichiometric solvates. In certain instances, the solvate will be capable of isolation, for example when one or more solvent molecules are incorporated in the crystal lattice of the crystalline solid. ‘Solvate’ encompasses both solution-phase and isolable solvates. Representative solvates include hydrates, ethanolates and methanolates.

The terms “inert solid diluent” or “solid diluent” or “diluents” refer to materials used to produce appropriate dosage form size, performance and processing properties for tablets and/or capsules. An inert solid diluent can be also referred to as filler or filler material. Particular examples of diluents include cellulose powdered, silicified microcrystalline cellulose acetate, compressible sugar, confectioner’s sugar, corn starch and pregelatinized starch, dextrates, dextrin, dextrose, erythritol, ethylcellulose, fructose, fumaric acid, glyceryl palmitostearate, inhalation lactose, isomalt, kaolin, lactitol, lactose, anhydrous, monohydrate and corn starch, spray dried monohydrate and microcrystalline cellulose, maltodextrin, maltose, mannitol, medium-chain triglycerides, microcrystalline cellulose, polydextrose, polymethacrylates, simethicone, sorbitol, pregelatinized starch, sterilizable maize, sucrose, sugar spheres, sulfobutylether β-cyclodextrin, talc, tragacanth, trehalose, or xylitol. More particular examples of diluents include cellulose powdered, silicified microcrystalline cellulose acetate, compressible sugar, corn starch and pregelatinized starch, dextrose, fructose, glyceryl palmitostearate, anhydrous, monohydrate and corn starch, spray dried monohydrate and microcrystalline cellulose, maltodextrin, maltose, mannitol, medium-chain triglycerides, microcrystalline cellulose, polydextrose, sorbitol, starch, pregelatinized, sucrose, sugar spheres, trehalose, or xylitol.

“Lubricant” refers to materials that prevent or reduce ingredients from clumping together and from sticking to the tablet punches or capsule filling machine. Lubricants also ensure that tablet formation and ejection can occur with low friction between the solid and die wall. Particular examples of lubricants include canola oil, hydrogenated castor oil, cottonseed oil, glyceryl behenate, glyceryl monostearate, glyceryl palmitostearate, medium-chain triglycerides, mineral oil, light mineral oil, octyldodecanol, poloxamer, polyethylene glycol, polyoxyethylene stearates, polyvinyl alcohol, starch, or hydrogenated vegetable oil. More particular examples of diluents include glyceryl behenate, glyceryl monostearate, or hydrogenated vegetable oil.

“Disintegrant” refers to material that dissolve when wet causing the tablet to break apart in the digestive tract, releasing the active ingredients for absorption. They ensure that when the tablet is in contact with water, it rapidly breaks down into smaller fragments, facilitating dissolution. Particular examples of disintegrants include alginic acid, powdered cellulose, chitosan, colloidal silicon dioxide, corn starch and pregelatinized starch, crospovidone, glycine, guar gum, low-substituted hydroxypropyl cellulose, methylcellulose, microcrystalline cellulose, or povidone.

The term “colorant” describes an agent that imparts color to a formulation. Particular examples of colorants include iron oxide, or synthetic organic dyes (US Food and Drug administration, Code of Federal Regulations, Title 21 CFR Part73, Subpart B).

The term “plasticizing agent” or “plasticizer” refers to an agent that is added to promote flexibility of films or coatings. Particular examples of plasticizing agent include polyethylene glycols or propylene glycol.

The term “pigment” in the context of the present invention refers to an insoluble coloring agent.

The term “film-coating agent’ or ‘coating agent’ or ‘coating material’ refers to an agent that is used to produce a cosmetic or functional layer on the outer surface of a dosage form. Particular examples of film-coating agent include glucose syrup, maltodextrin, alginates, or carrageenan.

“Glidant” refers to materials that are used to promote powder flow by reducing interparticle friction and cohesion. These are used in combination with lubricants as they have no ability to reduce die wall friction. Particular examples of glidants include powdered cellulose, colloidal silicon dioxide, hydrophobic colloidal silica, silicon dioxide, or talc. More particular examples of glidants include colloidal silicon dioxide, hydrophobic colloidal silica, silicon dioxide, or talc.

“Flavoring agents” refers to material that can be used to mask unpleasant tasting active ingredients and improve the acceptance that the patient will complete a course of medication. Flavorings may be natural (e.g., fruit extract) or artificial. Non limiting examples of flavoring agents include mint, cherry, anise, peach, apricot, licorice, raspberry, or vanilla.

The term “Subject” includes mammals such as humans. The terms “human”, “patient” and “subject” are used interchangeably herein.

“Effective amount” means the amount of a compound of the invention that, when administered to a subject for treating a disease, is sufficient to effect such treatment for the disease. The ‘effective amount’ can vary depending on the compound, the disease and its severity, and the age, weight, etc., of the subject to be treated.

“Preventing” or “prevention” refers to a reduction in risk of acquiring or developing a disease or disorder (i.e., causing at least one of the clinical symptoms of the disease not to develop in a subject that may be exposed to a disease-causing agent, or predisposed to the disease in advance of disease onset).

The term "prophylaxis" is related to "prevention", and refers to a measure or procedure the purpose of which is to prevent, rather than to treat or cure a disease. Non-limiting examples of prophylactic measures may include the administration of vaccines; the administration of low molecular weight heparin to hospital patients at risk for thrombosis due, for example, to immobilization; and the administration of an anti-malarial agent such as chloroquine, in advance of a visit to a geographical region where malaria is endemic or the risk of contracting malaria is high.

"Treating" or "treatment" of any disease or disorder refers, in one embodiment, to ameliorating the disease or disorder (i.e., arresting the disease or reducing the manifestation, extent or severity of at least one of the clinical symptoms thereof). In another embodiment "treating" or "treatment" refers to ameliorating at least one physical parameter, which may not be discernible by the subject. In yet another embodiment, "treating" or "treatment" refers to modulating the disease or disorder, either physically, (e.g., stabilization of a discernible symptom), physiologically, (e.g., stabilization of a physical parameter), or both. In a further embodiment, "treating" or "treatment" relates to slowing the progression of the disease.

As used herein, the term "isotopic variant" refers to a compound that contains unnatural proportions of isotopes at one or more of the atoms that constitute such compound. For example, an "isotopic variant" of a compound can contain one or more non-radioactive isotopes, such as for example, deuterium ($^2H$ or D), carbon-13 ($^{13}C$), nitrogen-15 ($^{15}N$), or the like. It will be understood that, in a compound where such isotopic substitution is made, the following atoms, where present, may vary, so that for example, any hydrogen may be $^2H$/D, any carbon may be $^{13}C$, or any nitrogen may be $^{15}N$, and that the presence and placement of such atoms may be determined within the skill of the art. Likewise, the invention may include the preparation of isotopic variants with radioisotopes, in the instance for example, where the resulting compounds may be used for drug and/or substrate tissue distribution studies. The radioactive isotopes tritium, i.e., $^3H$, and carbon-14, i.e. $^{14}C$, are particularly useful for this purpose in view of their ease of incorporation and ready means of detection. Further, compounds may be prepared that are substituted with positron emitting isotopes, such as $^{11}C$, $^{18}F$, $^{15}O$ and $^{13}N$, and would be useful in Positron, and 13 Emission Topography (PET) studies for examining substrate receptor occupancy.

All isotopic variants of the compounds provided herein, radioactive or not, are intended to be encompassed within the scope of the invention.

"Tautomers" refer to compounds that are interchangeable forms of a particular compound structure, and that vary in the displacement of hydrogen atoms and electrons. Thus, two structures may be in equilibrium through the movement of R electrons and an atom (usually H). For example, enols and ketones are tautomers because they are rapidly interconverted by treatment with either acid or base. Another example of tautomerism is the aci- and nitro-forms of phenylnitromethane, that are likewise formed by treatment with acid or base. Tautomeric forms may be relevant to the attainment of the optimal chemical reactivity and biological activity of a compound of interest.

The term "alkyl" as used herein, whether used alone or as part of another group, refers to a substituted or unsubstituted aliphatic hydrocarbon chain and includes, but is not limited to, straight and branched chains containing from 1 to 20 carbon atoms, preferably from 2 to 20, from 1 to 10, from 2 to 10, from 1 to 8, from 2 to 8, from 1 to 6, from 2 to 6, from 1 to 4, from 2 to 4, from 1 to 3 carbon atoms, unless explicitly specified otherwise. Illustrative alkyl groups can include, but are not limited to, methyl (Me), ethyl (Et), propyl (e.g., n-propyl and isopropyl), butyl (e.g., n-butyl, t-butyl, isobutyl), pentyl (e.g., n-pentyl, isopentyl, neopentyl), hexyl, isohexyl, heptyl, 4,4-dimethylpentyl, octyl, 2,2,4-trimethylpentyl, nonyl, decyl, undecyl, dodecyl, 2-methyl-1-propyl, 2-methyl-2-propyl, 2-methyl-1-butyl, 3-methyl-1-butyl, 2-methyl-3-butyl, 2-methyl-1-pentyl, 2,2-dimethyl-1-propyl, 3-methyl-1-pentyl, 4-methyl-1-pentyl, 2-methyl-2-pentyl, 3-methyl-2-pentyl, 4-methyl-2-pentyl, 2,2-dimethyl-1-butyl, 3,3-dimethyl-1-butyl, 2-ethyl-1-butyl, and the like.

The term "alkenyl" as used herein, whether used alone or as part of another group, refers to a substituted or unsubstituted aliphatic hydrocarbon chain and includes, but is not limited to, straight and branched chains having 2 to 8 carbon atoms and containing at least one carbon-carbon double bond.

The term "alkynyl" as used herein, whether used alone or as part of another group, refers to a substituted or unsubstituted aliphatic hydrocarbon chain and includes, but is not limited to, straight and branched chains having 1 to 6 carbon atoms and containing at least one carbon-carbon triple bond.

The term "alkoxy" as used herein, whether used alone or as part of another group, refers to alkyl-O— wherein alkyl is hereinbefore defined.

The term "cycloalkyl" as used herein, whether used alone or as part of another group, refers to a monocyclic, bicyclic, tricyclic, fused, bridged or spiro monovalent saturated hydrocarbon moiety, wherein the carbon atoms are located inside or outside of the ring system. Any suitable ring position of the cycloalkyl moiety may be covalently linked to the defined chemical structures. Illustrative cycloalkyl groups can include, but are not limited to, cyclopropyl, cyclopropylmethyl, cyclobutyl, cyclopentyl, cyclohexyl, cyclohexylmethyl, cyclohexylethyl, cycloheptyl, norbornyl, adamantly, spiro[4,5]decanyl, and homologs, isomers and the alike.

The term "aryl" as used herein, whether used alone or as part of another group, refers to an aromatic carbocyclic ring system having 6 to 30 carbon atoms, preferably 6 to 10 carbon atoms, optionally substituted with 1 to 3 substituents independently selected from halogen, nitro cyano, hydroxy, alkyl, alkenyl, alkoxy, cycloalkyl, amino, alkylamino, dialkylamino, carboxy, alkoxycarbonyl, haloalkyl, and phenyl.

The term "phenyl" as used herein, whether used alone or as part of another group, refers to a substituted or unsubstituted phenyl group.

The term "heteroaryl" as used herein, whether used alone or as part of another group, refers to a 3 to 30 membered aryl heterocyclic ring, which contains from 1 to 4 heteroatoms selected from the group consisting of O, N, Si, P and S atoms in the ring and may be fused with a carbocyclic or heterocyclic ring at any possible position.

The term "heterocycloalkyl" as used herein, whether used alone or as part of another group, refers to a 5 to 7 membered saturated ring containing carbon atoms and from 1 to 2 heteroatoms selected from the group consisting of O, N and S atoms.

The term "halogen or halo" as used herein, refers to fluoro, chloro, bromo or iodo.

The term "haloalkyl" as used herein, whether used alone or as part of another group, refers to an alkyl as hereinbefore defined, independently substituted with 1 to 3, F, Cl, Br or I.

The term "about" as used herein, refers that the numerical value is approximate and small variations would not significantly affect the practice of the disclosed embodiments. Where a numerical limitation is used, unless indicated otherwise by the context, “about” means the numerical value can vary by ±10% and remain within the scope of the disclosed embodiments. Additionally, in phrase “about X to Y,” is the same as “about X to about Y,” that is the term “about” modifies both “X” and “Y.”

The term “compound” as used herein, refers to salts, solvates, complexes, isomers, stereoisomers, diastereoisomers, tautomers, and isotopes of the compound or any combination thereof.

The term “comprising” (and any form of comprising, such as “comprise”, “comprises”, and “comprised”), “having” (and any form of having, such as “have” and “has”), “including” (and any form of including, such as “includes” and “include”), or “containing” (and any form of containing, such as “contains” and “contain”), are used in their inclusive, open-ended, and non-limiting sense.

The term “racemic” as used herein refers to a mixture of the (+) and (−) enantiomers of a compound wherein the (+) and (−) enantiomers are present in approximately a 1:1 ratio. The terms “substantially optically pure,” “optically pure,” and “optically pure enantiomers,” as used herein, mean that the composition contains greater than about 90% of a single stereoisomer by weight, preferably greater than about 95% of the desired enantiomer by weight, and more preferably greater than about 99% of the desired enantiomer by weight, based upon the total weight.

The term “enantiomer” refers to a stereoisomer that is a non-superimposable mirror image of each other. A diastereomer is a stereoisomer with two or more stereocenters, and the isomers are not mirror images of each other.

As used herein, the terms “gastrointestinal tract” and “gut” refer to the digestive tract from the stomach to the anus.

As used herein, the terms “bowel,” “intestine,” “intestines,” and “intestinal” can refer to the small intestine, the large intestine, or combinations thereof. The small intestine includes the duodenum, jejunum, and the ileum. The large intestine includes the cecum, the vermiform appendix, the colon, and the rectum. The colon includes the ascending colon, the traverse colon, the descending colon, and the sigmoid fixture.

As used herein, the term “intestinal mucosa” means glandular epithelium, lamina propria, and muscularis mucosa.

As used herein, the term “phosphodiesterase inhibitor” refers to a compound that inhibits one or more phosphodiesterases (PDE) “Inhibiting” a phosphodiesterase means to partially or completely reduce or inhibit the PDE from degrading intracellular second messengers’ cyclic adenosine monophosphate (cAMP), cyclic guanosine monophosphate (cGMP) or combinations thereof.

As used herein, the term “phosphodiesterase 5 inhibitor”, or “PDE5 inhibitor” means a compound that blocks the action of phosphodiesterase type 5, a cGMP specific phosphodiesterase.

As used herein, the term “prodrug” refers to a pharmacological substance (drug) which is administered in an inactive (or significantly less active) form. Once administered, the prodrug is metabolized in the body (in vivo) into the active compound.

As used herein, the terms “analog” and “derivative” are used herein interchangeably, and refer to a compound having a structure similar to that a parent compound, but varying from the parent compound by a difference in one or more certain components. The analog or derivative can differ from the parent compound in one or more atoms, functional groups, or substructures, which are replaced with other atoms, groups, or substructures. An analog or derivative can be imagined to be formed, at least theoretically, from the parent compound via some chemical or physical process.

II. Inhibitors of Gut-Specific Phosphodiesterase 5

Disclosed herein are first in class gut-localized phosphodiesterase 5 (PDE5) inhibitors that are designed to increase cGMP in the gut lining as a therapy for a spectrum of functional bowel disorders (FBD) and for the prevention of colorectal cancer (CRC).

In the next few years, contemporary PDE5 inhibitors such as Sildenafil, Vardenafil and Tadalafil are expected to become the first in class agents for CRC chemoprevention for the millions of men and women at high risk. These agents are currently prescribed for the treatment of erectile dysfunction, pulmonary arterial hypertension and benign prostate hyperplasia, but they have significant side effects (e.g. headache, flushing and dyspepsia) resulting from systemic delivery.

For CRC prevention, these side effects would reduce compliance in an otherwise healthy population. In addition, due to common predisposing factors, many high-risk CRC patients also take nitroglycerin to treat ischemic heart disease. These patients could not benefit from PDE5 inhibitors for CRC prevention due to drug-drug interactions.

Increasing intestinal cGMP levels using synthetic agonists of receptor guanylate cyclase C such as linaclotide and plecanatide are effective treatments for FBD including several forms of chronic constipation and gut pain. These agents aberrantly increase cGMP, which causes diarrhea as a common and intolerable side effect of this approach. PDE5 inhibitors do not cause diarrhea because they amplify endogenous guanylate cyclase agonists and do not cause aberrant cGMP elevation.

The contemporary (FDA approved) PDE5 inhibitors were specifically designed (using Lipinski’s rule of 5) to enter the bloodstream from the gut and travel to the target organs. The basis for this invention was to design PDE5 inhibitors to target GI diseases by adding chemical groups that reduce their movement into the circulation. One approach is to add highly polar residues that reduce the Log P value and the increase Topological Polar Surface Area of drug candidates.

A. Desmethyl Sildenafil Analogs

One embodiment provides a compound of Formula I:

Formula I

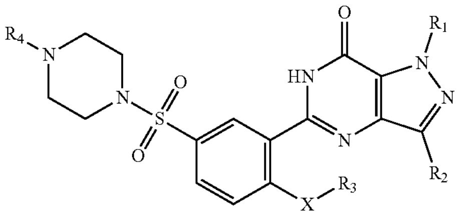

wherein $R_1$ and $R_2$ are each independently unsubstituted or substituted halogen, $C_{1-10}$ alkyl, $C_{1-10}$ alkoxy, $C_{3-10}$ cycloalkyl, aryl, and heteroaryl;

X is each independently —$CH_2$, —O, —S or —NH;

$R_3$ is independently unsubstituted or substituted OH, CN, COOH, $NO_2$, $NH_2$, $CONH_2$, $CH_2NH_2$, halogen, $C_{1-10}$ alkyl, $C_{1-10}$ alkoxy, $C_{3-10}$ cycloalkyl, aryl, and heteroaryl;

$R_4$ is independently unsubstituted or substituted H, OH, halogen, $C_{1-10}$ alkyl, $C_{1-10}$ alkoxy, $C_{3-10}$ cycloalkyl, aryl, heteroaryl, NCO, —$CH_2$-halogen, —CHO, —CN, $NO_2$, $NH_2$, —$CO(CH_2)_nNH_2$, —$CO(CH_2)_nNHR_6$, —$CO(CH_2)_nNR_6R_7$, —$COR_8$, —$COCHOHR_9$, —COOH, —$CH_2COOH$, —$COCH_2COOH$, —CO-$COR_{10}$, —$SO_2R_{11}$;

$R_6$ and $R_7$ are each independently H or unsubstituted or substituted $C_{1-10}$ alkyl;

$R_8$, $R_9$ and $R_{10}$ are each independently unsubstituted or substituted $C_{1-10}$ alkyl;

Ru is independently OH, ONa or $C_{1-10}$ alkyl, $NH_2$; and n is 1, 2, 3, 4, 5 or 6;

or a hydrate, enantiomer, tautomer, stereoisomers, solvate, zwitterion, polymorph, prodrug, or a pharmaceutically acceptable salt thereof.

In some embodiments, $R_1$, $R_2$ and $R_3$ are each independently $C_{1-10}$ alkyl.

In other embodiment, X is O.

In another embodiment, $R_4$ is $SO_2CH_3$.

In other embodiment, $R_4$ is $COCH_2COOH$.

In further embodiment, $R_4$ is —$COCH_2NH_2$, —$COCHCH_3NH_2$, —$COCH_2N(CH_3)_2$, —$COCH_2CH_2N(CH_3)_2$, —$COCH_2CH_2CH_3$, —$COCHOHCH_3$, or —CO-$COCH_3$.

In some embodiments, the compound is selected from the group consisting of

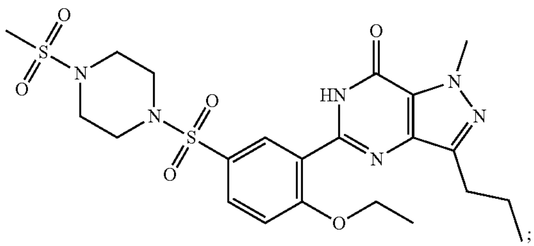

;

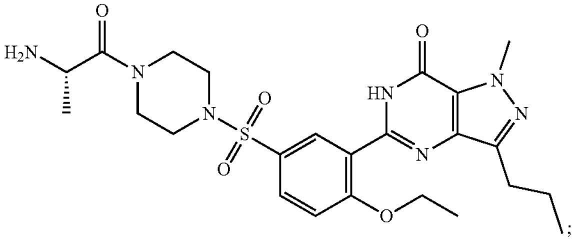

;

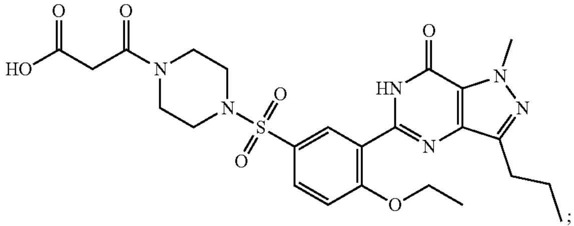

;

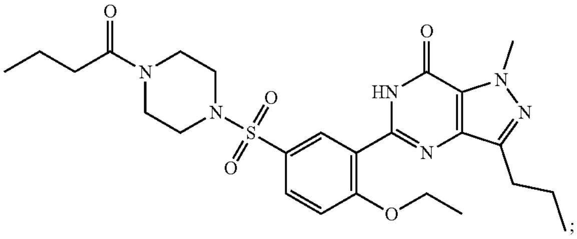

;

-continued

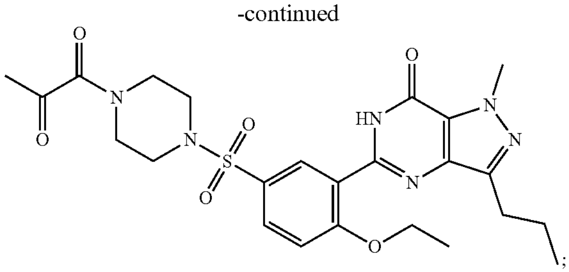

;

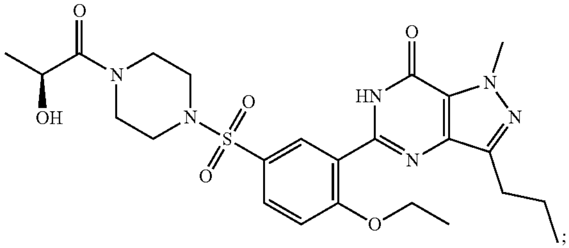

;

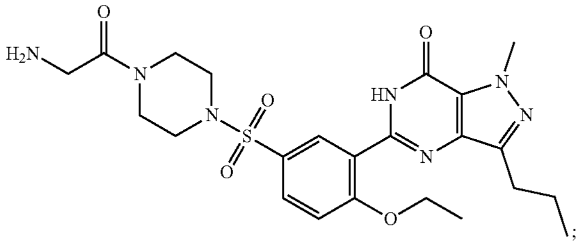

;

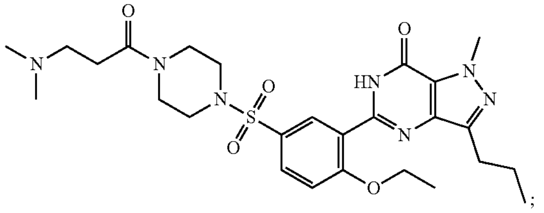

; and

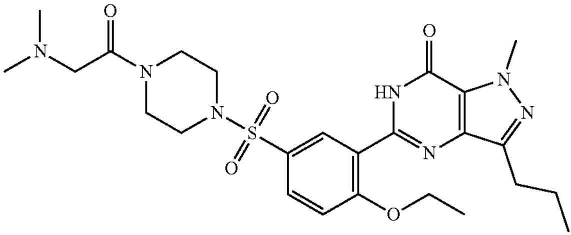

or a pharmaceutically acceptable salt thereof.

Figure 1B:
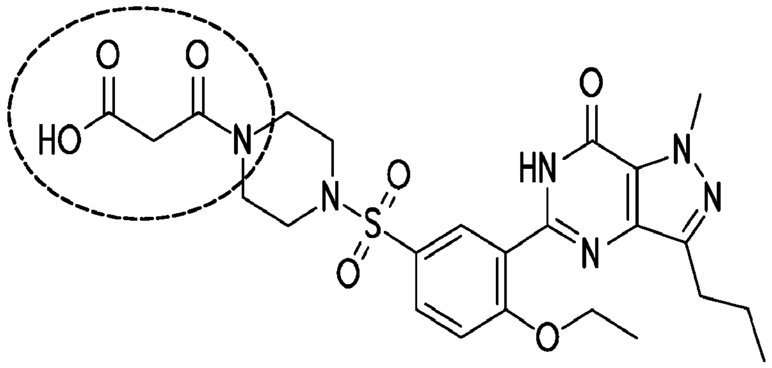
Figure 1C:
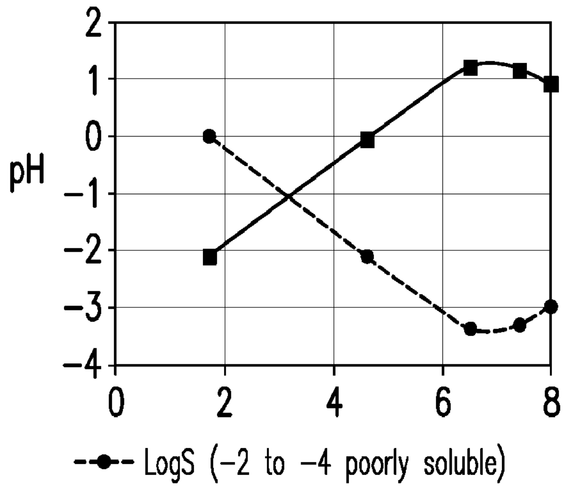
FIGS. 1C-1D show the effect of carboxylic acid substitution for methyl on sildenafil's permeability. The graphs show the theoretical calculations of solubility and permeability of the two compounds at different pH (chemicalize.com).
Figure 1D:
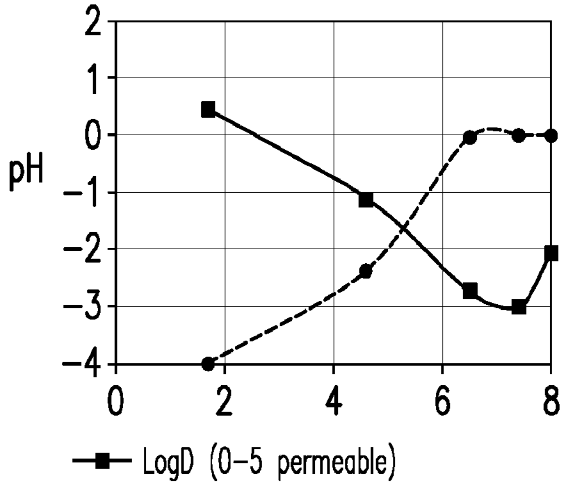

The PDE5 inhibitor compositions disclosed herein were designed by adding chemical groups that reduce their movement into the circulation. One approach adds highly polar residues that reduce the Log P value and increase Topological Polar Surface Area of drug candidates. In one embodiment, the compound is called malonyl-sildenafil and contains a carboxylic acid group that reduces permeability (log D; see FIG. 1B).

To develop gut-targeted (non-systemic) PDE5 inhibitors, the structure of the prototypical PDE5 inhibitor sildenafil was modified. Extensive structural studies of sildenafil have identified the piperazine nitrogen as amenable to modifications that affect pharmacokinetic properties without dramatically affecting pharmacological efficacy. In order to maximize the likelihood of developing non-systemic PDE5i, the foundational principles of medicinal chemistry were leveraged.

Most drugs take advantage of a set of chemical characteristics known as the Rule of 5 (Ro5) to optimize solubility and absorption into the circulation. The Ro5 principles use a value called Log D that measures polarity of the molecule at a given pH. More positive Log D values (0-5) favor leakage into circulation, while negative values indicate likely gut-retention. In one embodiment, the disclosed compositions have more negative Log D values and are retained in the gut.

A related measure is Log S, that measures relative solubility in the aqueous gut environment. More negative Log S values indicate lower solubility and increased likelihood a molecule will interact with plasma-membranes and leak into the circulation. In some embodiments, the disclosed compositions have more positive Log S and have a lower likelihood of leaking into circulation.

Sildenafil is a very effective drug because it epitomizes the hallmark Ro5 properties regarding overall size and lack of polarity that allow near-complete systemic delivery into the circulation. Post-gastric physiological pH is typically between 5-7, where sildenafil has positive Log D values and negative log S values that cause systemic delivery. Once in circulation, sildenafil undergoes hepatic modification into biologically active desmethyl-sildenafil (aka UK-103,320; FIG. 1).

Development of the disclosed malonyl-sildenafil compounds uses a "non-RO5" approach to generate PDE5 inhibitor structures that are charged at gastrointestinal pH. The approach with boronyl-sildenafil compound is that the BOH moiety forms transient covalent bonds that hinder its movement through tissues. Charged structures do not penetrate lipid membranes, and therefore do not enter systemic circulation by passive permeation through the intestinal epithelium (Charmot D. Curr Pharm Des 2012, 18:1434-1445; Fyfe MC. Elsevier, 2016, p. pp. 1-44; Johnson T W, Bioorg Med Chem Lett 2009, 19:5560-5564). To provide that charge, a carboxylic acid group was added for several reasons: (1) it provides the required charge at physiological pH, (2) this group has been reported to enhance PDE5i activity (Kim DK, Bioorg Med Chem 2001, 9:3013-3021) (3) it may serve as a possible target for monocarboxylate transporters that are expressed on the colon epithelium (Varma M, Current Drug Metabolism 2010, 11:730-742). In one embodiment, the carboxylic acid of one analog is derived from malonic acid (Malonyl-sildenafil) and another replaces the piperazine with a triazole containing a carboxylate (Triaz-COOH).

B. Prodrug Analogs

Other embodiment provides a compound of Formula II:

Formula II

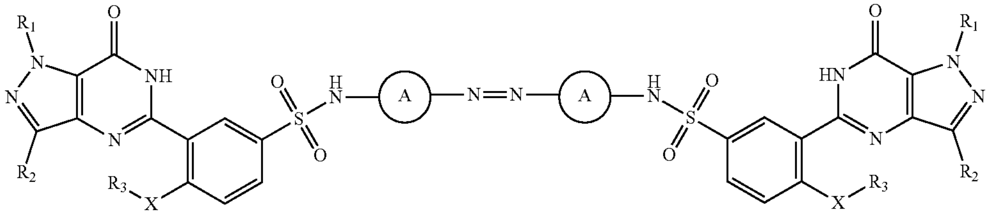

wherein $R_1$ and $R_2$ are each independently unsubstituted or substituted halogen, $C_{1-10}$ alkyl, $C_{1-10}$ alkoxy, $C_{3-10}$ cycloalkyl, aryl, and heteroaryl;

X is each independently —$CH_2$, —O, —S or —NH;

$R_3$ is independently unsubstituted or substituted OH, CN, COOH, $NO_2$, $NH_2$, $CONH_2$, $CH_2NH_2$, halogen, $C_{1-10}$ alkyl, $C_{1-10}$ alkoxy, $C_{3-10}$ cycloalkyl, aryl, and heteroaryl; and ring A is aryl, cycloalkyl or heteroaryl ring;

or a hydrate, enantiomer, tautomer, stereoisomers, solvate, zwitterion, polymorph, prodrug, or a pharmaceutically acceptable salt thereof.

In some embodiments, $R_1$, $R_2$ and $R_3$ are each independently $C_{1-10}$ alkyl.

In other embodiment, wherein X is O.

In another embodiment, wherein ring A is aryl ring.

In other embodiment, wherein ring A is heteroaryl ring.

In one embodiment, wherein ring A is pyridine ring.

In one embodiment, ring A is pyrimidine ring.

In some embodiments, the compound is selected from the group consisting of

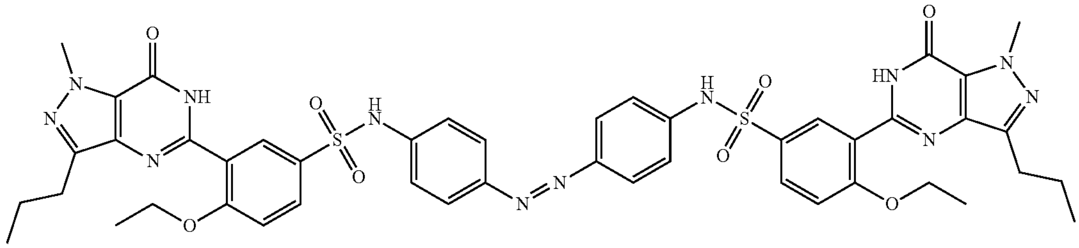

;

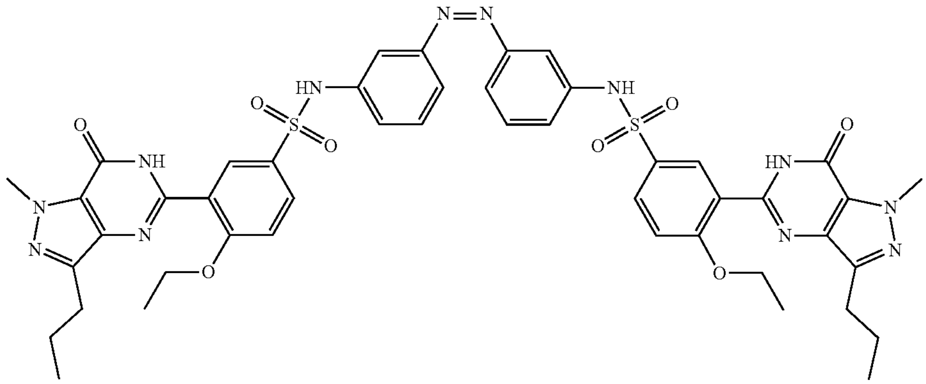

;

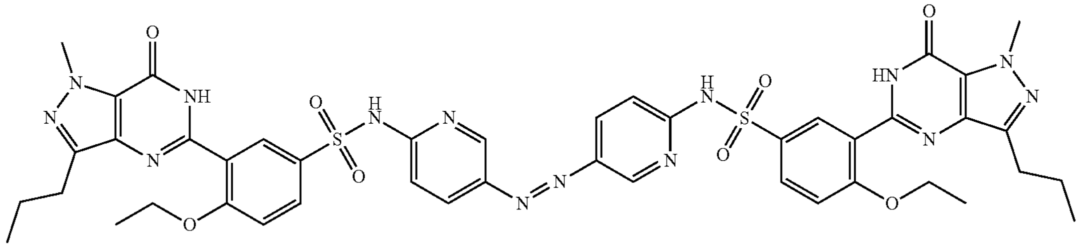

; and

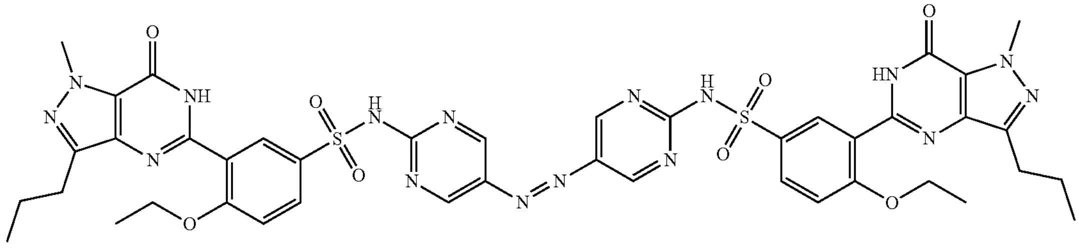

or a pharmaceutically acceptable salt thereof.

In other embodiment, the prodrug was designed that remain inactive until modified by enzymes expressed by intestinal bacteria. The first concept for a PDE5i prodrug that maintains the non-RO5 (Lipinski's rule of five and Veber rule for oral drugs) properties is a N-desmethyl Sildenafil-N-β-D-glucuronide. Taken orally, this structure is expected to release pharmacologically active desmethyl sildenafil (and inactive glucuronic acid) upon activation by β-glycosidases expressed in colonic bacteria.

In one embodiment, a unique prodrug structure that is novel in that it is a dimeric form of a sildenafil derivative containing an aromatic amino group. This drug takes advantage of bacterial azoreductases, which would generate two moles of the benz-amino sildenafil per mole of drug to effectively increase the colonic concentration. The large molecular weight of this compound is likely to support gut-retention despite the relative lack of polar groups. The benz-amino derivative that would be released to the colon has classical R05 properties that would facilitate entry into the target colonocytes.

C. Polar Non-Desmethyl Sildenafil Analogs

Another embodiment provides a compound of Formula III:

Formula III

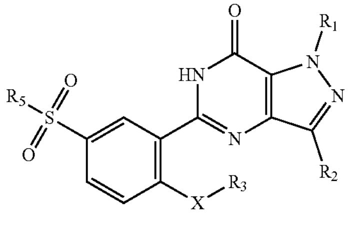

wherein

- $R_1$ and $R_2$ are each independently unsubstituted or substituted halogen, $C_{1-10}$ alkyl, $C_{1-10}$ alkoxy, $C_{3-10}$ cycloalkyl, aryl, and heteroaryl;
- X is each independently —$CH_2$, —O, —S or —NH;
- $R_3$ is independently unsubstituted or substituted OH, CN, COOH, $NO_2$, $NH_2$, $CONH_2$, $CH_2NH_2$, halogen, $C_{1-10}$ alkyl, $C_{1-10}$ alkoxy, $C_{3-10}$ cycloalkyl, aryl, and heteroaryl; and
- $R_5$ is independently unsubstituted or substituted H, OH, halogen, $C_{1-10}$ alkyl, $C_{1-10}$ alkoxy, $C_{3-10}$ cycloalkyl, aryl, heteroaryl, NCO, —$CH_2$-halogen, —CHO, —CN, —$NO_2$, —$NH_2$, —NH—, —NH—$C_{1-10}$ alkyl, —NH—$C_{1-10}$ alkoxy, —NH—$C_{3-10}$ cycloalkyl, —NH-aryl, —NH-heteroaryl, —COOH, —$CH_2COOH$, optionally substituted with —$B(OH)_2$, —CHO, —COOH, —$CH_2COOH$, —OH, —CN, —$SO_3H$, —$SO_3Na$, —$SO_2NH_2$, —$CH_3CO$, $NO_2$, $NH_2$, $CONH_2$, $CH_2NH_2$, halogen, $C_{1-10}$ alkyl, $C_{1-10}$ alkoxy, $C_{3-10}$ cycloalkyl, aryl, and heteroaryl, further optionally substituted with —COOH or —$SO_3H$;

or a hydrate, enantiomer, tautomer, stereoisomers, solvate, zwitterion, polymorph, prodrug, or a pharmaceutically acceptable salt thereof.

In some embodiments, $R_1$, $R_2$ and $R_3$ are each independently $C_{1-10}$ alkyl.

In other embodiment, X is O.

In another embodiment, $R_5$ is unsubstituted or substituted heteroaryl.

In further embodiment, heteroaryl is piperidine, pyridine, pyrimidine, imidazole, triazole or tetrazole.

In some embodiments, $R_5$ is heteroaryl optionally substituted with —$B(OH)_2$, —COOH, or —$SO_3H$.

In another embodiment, $R_5$ is NH optionally substituted with aryl or heteroaryl ring.

In some embodiments, the compound is selected from the group consisting of

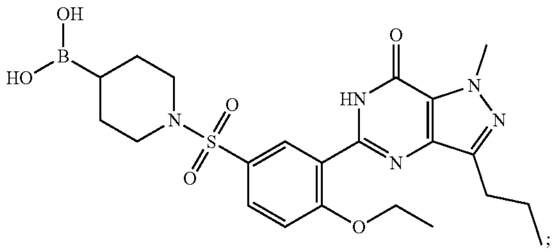

;

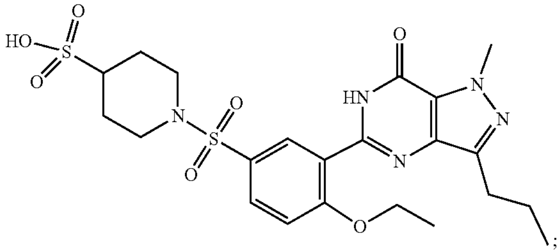

;

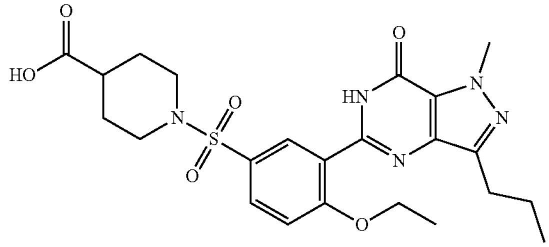

;

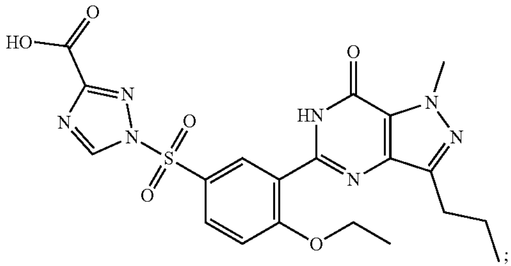

;

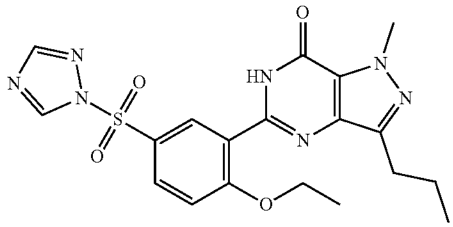

;

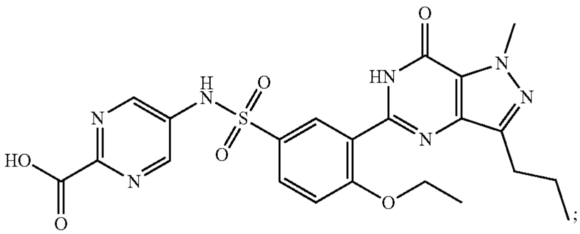

;

-continued

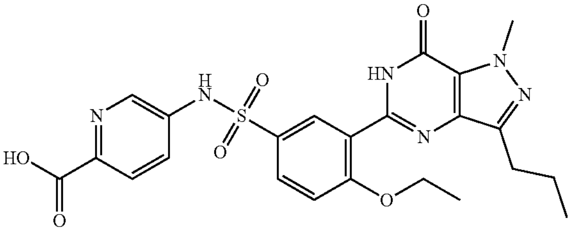

;

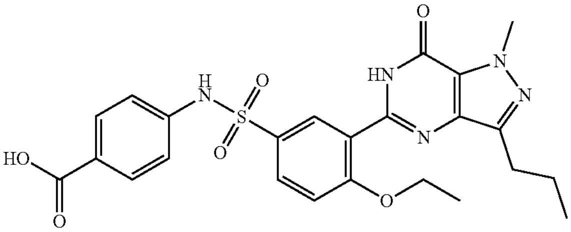

;

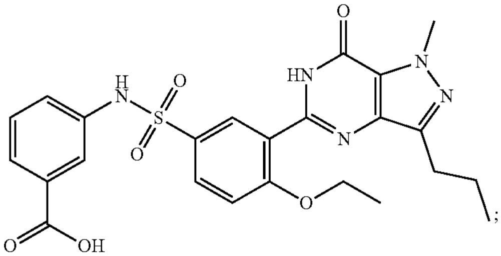

;

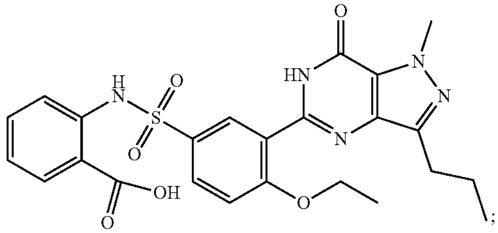

;

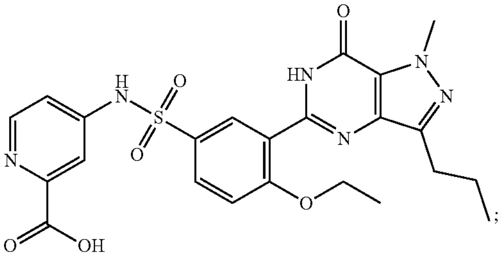

;

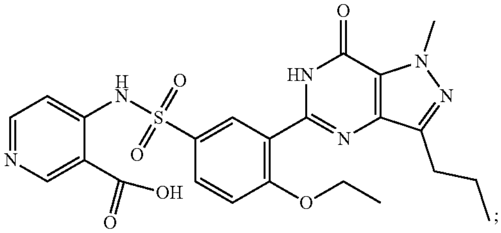

;

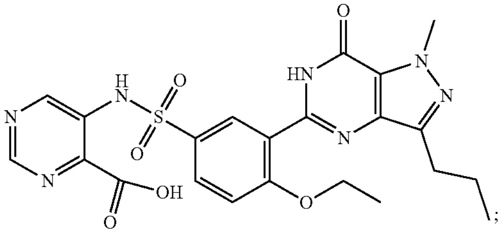

;

-continued

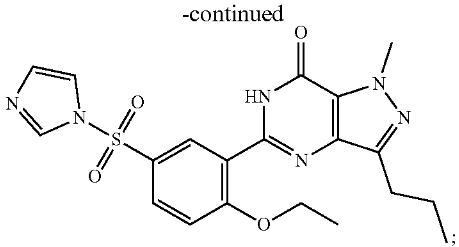

;

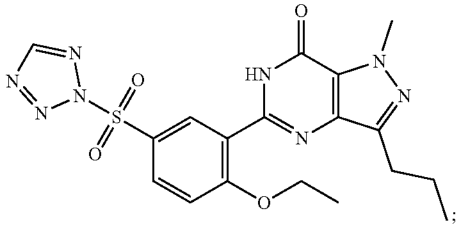

;

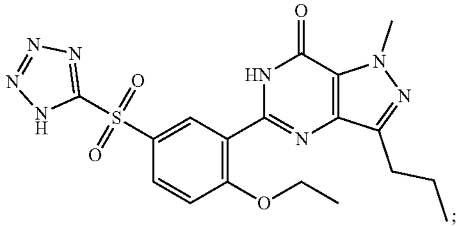

;

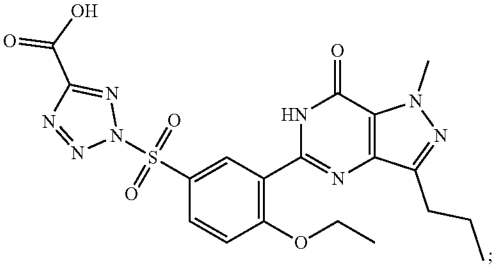

; and

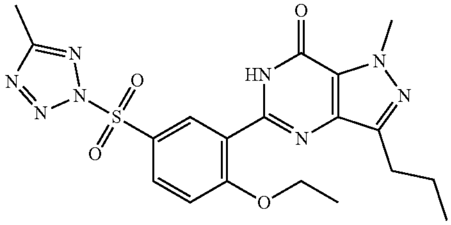

or a pharmaceutically acceptable salt thereof.

In some embodiment, the compound is a PDE5 inhibitor.

In other embodiment, the compound can enter intestinal epithelial cells.

In another embodiment, the compound is retained in the gastrointestinal tract.

In further embodiment, the compound reduces proliferation and increases differentiation of intestinal epithelial cells.

In one embodiment, the compound prevents colorectal cancer by reducing intestinal neoplasia.

In other embodiment, the compound increases intestinal barrier function.

III. Pharmaceutical Formulations

The compounds of Formula I, II or III and combinations thereof can be formulated into a pharmaceutical composition. The disclosed pharmaceutical compositions can be for formulated for administration by enteral, transdermal (either passively or using iontophoresis or electroporation), or rectal, routes of administration or using bioerodible inserts and can be formulated in dosage forms appropriate for each route of administration. The compositions can be administered systemically. Pharmaceutical compositions including an agent that inhibits the action of PDE5 and increase the level of cGMP in the intestinal mucosa are provided.

In one embodiment, the compounds of Formula I, II or III can be formulated for immediate release, extended release, or modified release. A delayed release dosage form is one that releases a drug (or drugs) at a time other than promptly after administration. An extended release dosage form is one that allows at least a twofold reduction in dosing frequency as compared to that drug presented as a conventional dosage form (e.g., as a solution or prompt drug-releasing, conventional solid dosage form). A modified release dosage form is one for which the drug release characteristics of time course and/or location are chosen to accomplish therapeutic or convenience objectives not offered by conventional dosage forms such as solutions, ointments, or promptly dissolving dosage forms. Delayed release and extended release dosage forms and their combinations are types of modified release dosage forms.

In some embodiments, the disclosed formulations are prepared using a pharmaceutically acceptable "carrier" composed of materials that are considered safe and effective and may be administered to an individual without causing undesirable biological side effects or unwanted interactions. The "carrier" is all components present in the pharmaceutical formulation other than the active ingredient or ingredients. The term "carrier" includes, but is not limited to, diluents, binders, lubricants, disintegrators, fillers, and coating compositions.

"Carrier" also includes all components of the coating composition which may include plasticizers, pigments, colorants, stabilizing agents, and glidants. The delayed release dosage formulations may be prepared as described in references such as "Pharmaceutical dosage form tablets", eds. Liberman et. al. (New York, Marcel Dekker, Inc., 1989), "Remington—The science and practice of pharmacy", 20th ed., Lippincott Williams & Wilkins, Baltimore, MD, 2000, and "Pharmaceutical dosage forms and drug delivery systems", $6^{th}$ Edition, Ansel et. al., (Media, PA: Williams and Wilkins, 1995) which provides information on carriers, materials, equipment and process for preparing tablets and capsules and delayed release dosage forms of tablets, capsules, and granules.

In one embodiment, the compounds of Formula I, II or III can be administered to a subject with or without the aid of a delivery vehicle. Appropriate delivery vehicles for the compounds are known in the art and can be selected to suit the particular active agent. For example, in some embodiments, the active agent(s) is/are incorporated into or encapsulated by, or bound to, a nanoparticle, microparticle, micelle, synthetic lipoprotein particle, or carbon nanotube. For example, the compositions can be incorporated into a vehicle such as polymeric microparticles which provide controlled release of the compounds of Formula I, II or III). In some embodiments, release of the compounds according to Formula I, II or III is controlled by diffusion of the compounds according to Formula I, II or III out of the microparticles and/or degradation of the polymeric particles by hydrolysis and/or enzymatic degradation.

Suitable polymers include ethylcellulose and other natural or synthetic cellulose derivatives. Polymers which are slowly soluble and form a gel in an aqueous environment, such as hydroxypropyl methylcellulose or polyethylene oxide, may also be suitable as materials for drug containing microparticles or particles. Other polymers include, but are not limited to, polyanhydrides, poly (ester anhydrides), polyhydroxy acids, such as polylactide (PLA), polyglycolide (PGA), poly(lactide-co-glycolide) (PLGA), poly-3-hydroxybut rate (PHB) and copolymers thereof, poly-4-hydroxybutyrate (P4HB) and copolymers thereof, polycaprolactone and copolymers thereof, and combinations thereof. In some embodiments, both agents are incorporated into the same particles and are formulated for release at different times and/or over different time periods. For example, in some embodiments, one of the agents is released entirely from the particles before release of the second agent begins. In other embodiments, release of the first agent begins followed by release of the second agent before the all of the first agent is released. In still other embodiments, both agents are released at the same time over the same period of time or over different periods of time.

A. Oral Immediate Release Formulations

Another embodiment provides suitable oral dosage forms containing of the compounds of Formula I, II or III that include but are not limited to tablets, capsules, solutions, suspensions, syrups, and lozenges. Tablets can be made using compression or molding techniques well known in the art. Gelatin or non-gelatin capsules can be prepared as hard or soft capsule shells, which can encapsulate liquid, solid, and semi-solid fill materials, using techniques well known in the art.

In a preferred embodiment, the compositions are formulated for oral delivery. Oral solid dosage forms are described generally in Remington's Pharmaceutical Sciences, 18th Ed. 1990 (Mack Publishing Co. Easton Pa. 18042) at Chapter 89. Solid dosage forms include tablets, capsules, pills, troches or lozenges, cachets, pellets, powders, or granules or incorporation of the material into particulate preparations of polymeric compounds such as polylactic acid, polyglycolic acid, etc. or into liposomes. Such compositions may influence the physical state, stability, rate of in vivo release, and rate of in vivo clearance of the disclosed. See, e.g., Remington's Pharmaceutical Sciences, 18th Ed. (1990, Mack Publishing Co., Easton, Pa. 18042) pages 1435-1712 which are herein incorporated by reference. The compositions may be prepared in liquid form, or may be in dried powder (e.g., lyophilized) form. Liposomal or proteinoid encapsulation may be used to formulate the compositions. Liposomal encapsulation may be used and the liposomes may be derivatized with various polymers (e.g., U.S. Pat. No. 5,013,556). See also Marshall, K. In: Modern Pharmaceutics Edited by G. S. Banker and C. T. Rhodes Chapter 10, 1979. In general, the formulation will include the peptide (or chemically modified forms thereof) and inert ingredients which protect peptide in the stomach environment, and release of the biologically active material in the intestine.

Another embodiment provides liquid dosage forms for oral administration, including pharmaceutically acceptable emulsions, solutions, suspensions, and syrups, which may contain other components including inert diluents; adjuvants such as wetting agents, emulsifying and suspending agents; and sweetening, flavoring, and perfuming agents.

Controlled release oral formulations may be desirable. An agent that increases the level of cGMP in the intestinal mucosa can be incorporated into an inert matrix which permits release by either diffusion or leaching mechanisms, e.g., gums. Slowly degenerating matrices may also be incorporated into the formulation. Another form of a controlled release is based on the Oros therapeutic system (Alza Corp.), i.e. the drug is enclosed in a semipermeable membrane which allows water to enter and push drug out through a single small opening due to osmotic effects.

For oral formulations, the location of release may be the stomach, the small intestine (the duodenum, the jejunum, or the ileum), or the large intestine. Preferably, the release will avoid the deleterious effects of the stomach environment, either by protection of the agent (or derivative) or by release of the agent (or derivative) beyond the stomach environment, such as in the intestine. To ensure full gastric resistance a coating impermeable to at least pH 5.0 is essential. Examples of the more common inert ingredients that are used as enteric coatings are cellulose acetate trimellitate (CAT), hydroxypropylmethylcellulose phthalate (HPMCP), HPMCP 50, HPMCP 55, polyvinyl acetate phthalate (PVAP), Eudragit L30D™, Aquateric™ cellulose acetate phthalate (CAP), Eudragit L™, Eudragit S™, and Shellac™. These coatings may be used as mixed films.

For the disclosed compounds, as further studies are conducted, information will emerge regarding appropriate dosage levels for treatment of various conditions in various patients, and the ordinary skilled worker, considering the therapeutic context, age, and general health of the recipient, will be able to ascertain proper dosing. The selected dosage depends upon the desired therapeutic effect, on the route of administration, and on the duration of the treatment desired. Generally, dosage levels of 0.1 to 100 mg/kg of body weight daily are administered to mammals. In one embodiment, dosage levels of 1 mg/kg to 50 mg/kg of body weight daily are administered. In another embodiment, dosage levels of 5 mg/kg to 35 mg/kg of body weight daily are administered.

Examples of suitable coating materials include, but are not limited to, cellulose polymers such as cellulose acetate phthalate, hydroxypropyl cellulose, hydroxypropyl methylcellulose, hydroxypropyl methylcellulose phthalate and hydroxypropyl methylcellulose acetate succinate; polyvinyl acetate phthalate, acrylic acid polymers and copolymers, and methacrylic resins that are commercially available under the trade name Eudragit® (Roth Pharma, Westerstadt, Germany), Zein, shellac, and polysaccharides.

Additionally, the coating material may contain conventional carriers such as plasticizers, pigments, colorants, glidants, stabilization agents, pore formers and surfactants.

Optional pharmaceutically acceptable excipients present in the drug-containing tablets, beads, granules or particles include, but are not limited to, diluents, binders, lubricants, disintegrants, colorants, stabilizers, and surfactants. Diluents, also termed "fillers," are typically necessary to increase the bulk of a solid dosage form so that a practical size is provided for compression of tablets or formation of beads and granules. Suitable diluents include, but are not limited to, dicalcium phosphate dihydrate, calcium sulfate, lactose, sucrose, mannitol, sorbitol, cellulose, microcrystalline cellulose, kaolin, sodium chloride, dry starch, hydrolyzed starches, pregelatinized starch, silicone dioxide, titanium oxide, magnesium aluminum silicate and powder sugar.

In some embodiments, binders are used to impart cohesive qualities to a solid dosage formulation, and thus ensure that a tablet or bead or granule remains intact after the formation of the dosage forms. Suitable binder materials include, but are not limited to, starch, pregelatinized starch, gelatin, sugars (including sucrose, glucose, dextrose, lactose and sorbitol), polyethylene glycol, waxes, natural and synthetic gums such as acacia, tragacanth, sodium alginate, cellulose, including hydroxypropylmethylcellulose, hydroxypropylcellulose, ethylcellulose, and veegum, and synthetic polymers such as acrylic acid and methacrylic acid copolymers, methacrylic acid copolymers, methyl methacrylate copolymers, aminoalkyl methacrylate copolymers, polyacrylic acid/polymethacrylic acid and polyvinylpyrrolidone.

In some embodiments, lubricants are used to facilitate tablet manufacture. Examples of suitable lubricants include, but are not limited to, magnesium stearate, calcium stearate, stearic acid, glycerol behenate, polyethylene glycol, talc, and mineral oil.

Disintegrants are used to facilitate dosage form disintegration or "breakup" after administration, and generally include, but are not limited to, starch, sodium starch glycolate, sodium carboxymethyl starch, sodium carboxymethylcellulose, hydroxypropyl cellulose, pregelatinized starch, clays, cellulose, alginine, gums or cross linked polymers, such as cross-linked PVP (Polyplasdone XL from GAF Chemical Corp).

In some embodiments, stabilizers are used to inhibit or retard drug decomposition reactions which include, by way of example, oxidative reactions.

Some embodiments include surfactants. The surfactants may be anionic, cationic, amphoteric or nonionic surface active agents. Suitable anionic surfactants include, but are not limited to, those containing carboxylate, sulfonate and sulfate ions. Examples of anionic surfactants include sodium, potassium, ammonium of long chain alkyl sulfonates and alkyl aryl sulfonates such as sodium dodecylbenzene sulfonate; dialkyl sodium sulfosuccinates, such as sodium dodecylbenzene sulfonate; dialkyl sodium sulfosuccinates, such as sodium bis-(2-ethylthioxyl)-sulfosuccinate; and alkyl sulfates such as sodium lauryl sulfate. Cationic surfactants include, but are not limited to, quaternary ammonium compounds such as benzalkonium chloride, benzethonium chloride, cetrimonium bromide, stearyl dimethylbenzyl ammonium chloride, polyoxyethylene and coconut amine. Examples of nonionic surfactants include ethylene glycol monostearate, propylene glycol myristate, glyceryl monostearate, glyceryl stearate, polyglyceryl-4-oleate, sorbitan acylate, sucrose acylate, PEG-150 laurate, PEG-400 monolaurate, polyoxyethylene monolaurate, polysorbates, polyoxyethylene octylphenylether, PEG-1000 cetyl ether, polyoxyethylene tridecyl ether, polypropylene glycol butyl ether, POLOXAMER® 401, stearoyl monoisopropanolamide, and polyoxyethylene hydrogenated tallow amide. Examples of amphoteric surfactants include sodium N-dodecyl-.beta.-alanine, sodium N-lauryl-.beta.-iminodipropionate, myristoamphoacetate, lauryl betaine and lauryl sulfobetaine.

If desired, the tablets, beads granules or particles may also contain minor amount of nontoxic auxiliary substances such as wetting or emulsifying agents, dyes, pH buffering agents, and preservatives.

B. Extended Release Dosage Forms

One embodiment provides extended release formulations of compounds of Formula I, II or III that are generally prepared as diffusion or osmotic systems, for example, as described in "Remington—The science and practice of pharmacy" (20th ed., Lippincott Williams & Wilkins, Baltimore, MD, 2000). A diffusion system typically consists of two types of devices, reservoir and matrix, and is well known and described in the art. The matrix devices are generally prepared by compressing the drug with a slowly dissolving polymer carrier into a tablet form. The three major types of materials used in the preparation of matrix devices are insoluble plastics, hydrophilic polymers, and fatty compounds. Plastic matrices include, but not limited to, methyl acrylate-methyl methacrylate, polyvinyl chloride, and polyethylene. Hydrophilic polymers include, but are not limited to, methylcellulose, hydroxypropylcellulose, hydroxypropylmethylcellulose, sodium carboxymethylcellulose, and carbopol 934, polyethylene oxides. Fatty compounds include, but are not limited to, various waxes such as carnauba wax and glyceryl tristearate.

Alternatively, extended release formulations of the compounds of Formulas I, II or III can be prepared using osmotic systems or by applying a semi-permeable coating to the dosage form. In the latter case, the desired drug release profile can be achieved by combining low permeable and high permeable coating materials in suitable proportion.

The devices with different drug release mechanisms described above could be combined in a final dosage form comprising single or multiple units. Examples of multiple units include multilayer tablets, capsules containing tablets, beads, granules, etc.

An immediate release portion can be added to the extended release system by means of either applying an immediate release layer on top of the extended release core using coating or compression process or in a multiple unit system such as a capsule containing extended and immediate release beads.

Extended release tablets containing hydrophilic polymers are prepared by techniques commonly known in the art such as direct compression, wet granulation, or dry granulation processes. Their formulations usually incorporate polymers, diluents, binders, and lubricants as well as the active pharmaceutical ingredient. The usual diluents include inert powdered substances such as any of many different kinds of starch, powdered cellulose, especially crystalline and microcrystalline cellulose, sugars such as fructose, mannitol and sucrose, grain flours and similar edible powders. Typical diluents include, for example, various types of starch, lactose, mannitol, kaolin, calcium phosphate or sulfate, inorganic salts such as sodium chloride and powdered sugar. Powdered cellulose derivatives are also useful. Typical tablet binders include substances such as starch, gelatin and sugars such as lactose, fructose, and glucose. Natural and synthetic gums, including acacia, alginates, methylcellulose, and polyvinylpyrrolidine can also be used. Polyethylene glycol, hydrophilic polymers, ethylcellulose and waxes can also serve as binders. A lubricant is necessary in a tablet formulation to prevent the tablet and punches from sticking in the die. The lubricant is chosen from such slippery solids as talc, magnesium and calcium stearate, stearic acid and hydrogenated vegetable oils.

Extended release tablets containing wax materials are generally prepared using methods known in the art such as a direct blend method, a congealing method, and an aqueous dispersion method. In a congealing method, the drug is mixed with a wax material and either spray-congealed or congealed and screened and processed.

C. Delayed Release Dosage Forms

In some embodiments delayed release formulations of compounds of Formula I are created by coating a solid dosage form with a film of a polymer which is insoluble in the acid environment of the stomach, and soluble in the neutral environment of small intestines.

The delayed release dosage units can be prepared, for example, by coating a drug or a drug-containing composition with a selected coating material. The drug-containing composition may be, e.g., a tablet for incorporation into a capsule, a tablet for use as an inner core in a "coated core" dosage form, or a plurality of drug-containing beads, particles or granules, for incorporation into either a tablet or capsule. Preferred coating materials include bioerodible, gradually hydrolyzable, gradually water-soluble, and/or enzymatically degradable polymers, and may be conventional "enteric" polymers. Enteric polymers, as will be appreciated by those skilled in the art, become soluble in the higher pH environment of the lower gastrointestinal tract or slowly erode as the dosage form passes through the gastrointestinal tract, while enzymatically degradable polymers are degraded by bacterial enzymes present in the lower gastrointestinal tract, particularly in the colon. Suitable coating materials for effecting delayed release include, but are not limited to, cellulosic polymers such as hydroxypropyl cellulose, hydroxyethyl cellulose, hydroxymethyl cellulose, hydroxypropyl methyl cellulose, hydroxypropyl methyl cellulose acetate succinate, hydroxypropylmethyl cellulose phthalate, methylcellulose, ethyl cellulose, cellulose acetate, cellulose acetate phthalate, cellulose acetate trimellitate and carboxymethylcellulose sodium; acrylic acid polymers and copolymers, preferably formed from acrylic acid, methacrylic acid, methyl acrylate, ethyl acrylate, methyl methacrylate and/or ethyl methacrylate, and other methacrylic resins that are commercially available under the tradename EUDRAGIT®. (Rohm Pharma; Westerstadt, Germany), including EUDRAGIT®. L30D-55 and L100-55 (soluble at pH 5.5 and above), EUDRAGIT®. L-100 (soluble at pH 6.0 and above), EUDRAGIT®. S (soluble at pH 7.0 and above, as a result of a higher degree of esterification), and EUDRAGITS®. NE, RL and RS (water-insoluble polymers having different degrees of permeability and expandability); vinyl polymers and copolymers such as polyvinyl pyrrolidone, vinyl acetate, vinylacetate phthalate, vinylacetate crotonic acid copolymer, and ethylene-vinyl acetate copolymer; enzymatically degradable polymers such as azo polymers, pectin, chitosan, amylose and guar gum; zein and shellac. Combinations of different coating materials may also be used. Multilayer coatings using different polymers may also be applied.

The preferred coating weights for particular coating materials may be readily determined by those skilled in the art by evaluating individual release profiles for tablets, beads and granules prepared with different quantities of various coating materials. It is the combination of materials, method and form of application that produce the desired release characteristics, which one can determine only from the clinical studies.

The coating composition may include conventional additives, such as plasticizers, pigments, colorants, stabilizing agents, glidants, etc. A plasticizer is normally present to reduce the fragility of the coating, and will generally represent about 10 wt. % to 50 wt. % relative to the dry weight of the polymer. Examples of typical plasticizers include polyethylene glycol, propylene glycol, triacetin, dimethyl phthalate, diethyl phthalate, dibutyl phthalate, dibutyl sebacate, triethyl citrate, tributyl citrate, triethyl acetyl citrate, castor oil and acetylated monoglycerides. A stabilizing agent is preferably used to stabilize particles in the dispersion. Typical stabilizing agents are nonionic emulsifiers such as sorbitan esters, polysorbates and polyvinylpyrrolidone. Glidants are recommended to reduce sticking effects during film formation and drying, and will generally represent approximately 25 wt. % to 100 wt. % of the polymer weight in the coating solution. One effective glidant is talc. Other glidants such as magnesium stearate and glycerol monostearates may also be used. Pigments such as titanium dioxide may also be used. Small quantities of an anti-foaming agent, such as a silicone (e.g., simethicone), may also be added to the coating composition.

D. Transdermal Formulations

Transdermal formulations containing the compounds of Formula I, II or III may also be prepared. Transdermal formulations can include rectal or colonic delivery by enema.

E. Methods of Manufacture

As will be appreciated by those skilled in the art and as described in the pertinent texts and literature, a number of methods are available for preparing formulations containing the compounds of Formula I, II or III including but not limited to tablets, beads, granules, microparticle, or nanoparticles that provide a variety of drug release profiles. Such methods include, but are not limited to, the following: coating a drug or drug-containing composition with an appropriate coating material, typically although not necessarily incorporating a polymeric material, increasing drug particle size, placing the drug within a matrix, and forming complexes of the drug with a suitable complexing agent.

The delayed release dosage units may be coated with the delayed release polymer coating using conventional techniques, e.g., using a conventional coating pan, an airless spray technique, fluidized bed coating equipment (with or without a Wurster insert). For detailed information concerning materials, equipment and processes for preparing tablets and delayed release dosage forms, see Pharmaceutical Dosage Forms: Tablets, eds. Lieberman et al. (New York: Marcel Dekker, Inc., 1989), and Ansel et al., Pharmaceutical Dosage Forms and Drug Delivery Systems, 6.sup.th Ed. (Media, PA: Williams & Wilkins, 1995).

An exemplary method for preparing extended release tablets includes compressing a drug-containing blend, e.g., blend of drug-containing granules, prepared using a direct blend, wet-granulation, or dry-granulation process. Extended release tablets may also be molded rather than compressed, starting with a moist material containing a suitable water-soluble lubricant. However, tablets are preferably manufactured using compression rather than molding. A preferred method for forming extended release drug-containing blend is to mix drug particles directly with one or more excipients such as diluents (or fillers), binders, disintegrants, lubricants, glidants, and colorants. As an alternative to direct blending, a drug-containing blend may be prepared by using wet-granulation or dry-granulation processes. Beads containing the active agent may also be prepared by any one of a number of conventional techniques, typically starting from a fluid dispersion. For example, a typical method for preparing drug-containing beads involves dispersing or dissolving the active agent in a coating suspension or solution containing pharmaceutical excipients such as polyvinylpyrrolidone, methylcellulose, talc, metallic stearates, silicone dioxide, plasticizers or the like. The admixture is used to coat a bead core such as a sugar sphere (or so-called "non-pareil") having a size of approximately 60 to 20 mesh.

An alternative procedure for preparing drug beads is by blending drug with one or more pharmaceutically acceptable excipients, such as microcrystalline cellulose, lactose, cellulose, polyvinyl pyrrolidone, talc, magnesium stearate, a disintegrant, etc., extruding the blend, spheronizing the extrudate, drying and optionally coating to form the immediate release beads.

IV. Methods of Use

The compounds of Formula I, II or III and pharmaceutical compositions thereof are useful for the treatment of an PDE5-related disease, disorder or condition. In some embodiments, the PDE5-related disease, disorder or condition is intestinal or bowel disorder. Another embodiment provides methods of inhibiting PDE5 in a subject in need thereof by contacting the subject's cells expressing PDE5 with an effective amount of a compound of Formula I, II or III or a pharmaceutical composition thereof. Another embodiment provides a method of preventing or slowing the development of colorectal cancer in a subject in need thereof by administering to the subject a therapeutically effective amount of the compound of Formula I, II or III or a pharmaceutical composition thereof that increases cellular level of cGMP in the intestinal mucosa to reduce intestinal neoplasia.

The compositions disclosed herein are useful for treating one or more symptoms of chronic constipation, inflammatory bowel disease, for preventing intestinal cancer, and for increasing intestinal luminal integrity. In some embodiments, the compositions are used to treat a disease or disorder of the gastrointestinal tract. In some embodiments, the compositions are used to treat diseases and disorders of the large intestine, for example, the colon, or a sub-region thereof such as the ascending colon, the traverse colon, the descending colon, the sigmoid fixture, the rectum, or combinations thereof. In certain embodiment, the composition is only active in a specific region or sub-region of the gastrointestinal tract, for example, the small intestine or the large intestine. In some embodiments, the composition is targeted to a specific region or sub-region of the gastrointestinal tract.

In one embodiment, the disclosed compositions exert their activity in the intestinal tract. The compositions were designed to stay within the intestinal tract and not enter systemic circulation. In one embodiment, the compositions have reduced, or minimal systemic delivery compared to existing phosphodiesterase inhibitors.

Without being bound by any one theory, it is believed that cGMP produced in the intestinal epithelium is pumped out via a transporter into the lamina propria, where it interacts with both afferent nerves (for constipation and IBS treatment), and possibly resident immune cells (treatment of colitis). In one embodiment, the transporter is the multidrug transporter MDR4. some anti-inflammatory effects on resident macrophages and a neuronal dampening effect on resident afferent fibers that can affect both motility and nociception.

A. Intestinal and Bowel Disorders

In one embodiment, the composition that inhibits PDE5 in the gut and increase the level of cGMP in the intestinal mucosa can be used to reduce or alleviate one or more symptoms of an intestinal or bowel disease or disorder. The disclosed compositions can be administered to a subject in need thereof in an amount effective to increase the level of cGMP in the intestinal mucosa for example in intestinal epithelial cells. In a preferred embodiment, one of the disclosed compositions is administered to patient in need thereof in an amount effective to reduce one or more symptoms of the intestinal or bowel disease or disorder. In an embodiment, the composition will not enter systemic circulation and will be excreted. In one embodiment, the disclosed compounds increase cGMP in the intestinal epithelium to activate intrinsic PKG, or pump cGMP into the lamina propria to affect resident cells.

Intestinal and bowel disorders include inflammatory bowel disorders. Representative inflammatory bowel disorders include but are not limited to inflammatory bowel diseases such as Crohn's disease, ulcerative colitis, necrotizing enterocolitis, collagenous colitis, lymphocytic colitis, ischaemic colitis, diversion colitis, Behçet's disease, and indeterminate colitis. Symptoms of inflammatory disorders include, but are not limited to, abdominal pain, vomiting, diarrhea, rectal bleeding, severe internal cramps/muscle spasms in the region of the pelvis, weight loss, arthritis, pyoderma gangrenosum, and primary sclerosing cholangitis. Intestinal and bowel disorders also include conditions such as irritable bowel syndrome (IBS) which is a functional bowel disorder characterized by chronic abdominal pain, discomfort, bloating, and alteration of bowel habits. Symptoms of patients suffering from IBS include, but are not limited to, abdominal pain or discomfort, frequent diarrhea or constipation, a change in bowel habits, urgency for bowel movements, a feeling of incomplete evacuation (tenesmus), bloating or abdominal distention, gastroesophageal reflux, symptoms relating to the genitourinary system, chronic fatigue syndrome, fibromyalgia, headache, and backache.

Other intestinal disorders that can be treated using the disclosed compositions include gastroenteritis, ileitis, appendicitis, and coeliac disease.

B. Cancer

In other embodiment, composition that inhibits PDE5 in the gut and increase the level of cGMP in the intestinal mucosa or increase the activity of a PKG, preferably PKG2, in the intestinal mucosa, can be used to reduce or alleviate one or more symptoms of cancer or to prevent the development of new cancer in the gut. In a preferred embodiment, the disclosed compositions are used to prevent an intestinal cancer. Intestinal cancers including, but not limited to, duodenal cancer, ileal cancer, jejunal cancer, small intestine cancer, and colon (colorectal) cancer. The disclosed compositions can be administered to a subject in need thereof in an effective amount to inhibit PDE5 and increase the level of cGMP in the intestinal mucosa or increase the activity of a PKG, preferably PKG2, in the intestinal mucosa, for example, in intestinal epithelial cells.

In another embodiment, one of the disclosed phosphodiesterase inhibitor compositions is administered to a subject in need thereof in an amount effective to reduce one or more symptoms of the intestinal cancer. For example, in some embodiments, treatment results in a reduced number of tumor cells or tumor burden. In some embodiments, the number of tumor cells or tumor burden is not increased.

In a preferred embodiment, one of the disclosed phosphodiesterase inhibitor composition is administered to a subject in need thereof in an amount effective to prevent or delay the onset of colorectal cancer. In some embodiments, the patient in need thereof will have a genetic predisposition to colorectal cancer such as by not limited to Lynch syndrome (hereditary non-polyposis colorectal cancer), familial adenomatous polyposis syndrome, or juvenile polyposis syndrome. In another embodiment, the subject in need thereof is at a higher risk for colon cancer because of a family history, previous polypectomy, or due to diagnosis of inflammatory bowel disease, such as Crohn's disease or ulcerative colitis. In one embodiment, previous family history includes but is not limited to a $1^{st}$ person relative being diagnosed, particularly at a young age, such as younger than 50 years old.

C. Improving Luminal Barrier Integrity

Increased intestinal permeability, or leaky guy syndrome, allows partially digested food, toxins, and bacteria to penetrate the tissues beneath it. This may trigger inflammation and changes in the gut flora (normal bacteria) that could lead to problems within the digestive tract and beyond.

It has been discovered that cGMP activity participates in intestinal homeostasis. Therefore, the disclosed compounds that inhibit PDE5 and increase the level of cGMP in the intestinal mucosa can be used to reduce or alleviate one or more pathologies of the intestinal mucosa.

The intestinal epithelium provides a barrier between antigenic luminal contents and the underlying immune cells. As used herein, "intestinal luminal integrity," refers to the ability of the intestinal luminal surface to prevent or inhibit antigens and microbial metabolites in the lumen of the gastrointestinal tract from penetrating the luminal surface and accessing the underling immune cells. Intestinal mucosa with increased or improved luminal integrity is able to withstand more or greater insults or exhibit greater protection from luminal antigens.

Luminal integrity can include, but is not limited to, an intact mucosa at the luminal surface and a protective mucus barrier that separates the epithelial surface from luminal contents. It has been discovered that cGMP activity contributes to luminal integrity of the intestinal mucosa. Therefore, composition that inhibits PDE5 and increase the level of cGMP in the intestinal mucosa increase or improve luminal integrity. In some embodiments, the luminal surface of the intestinal mucosa of a subject who has been administered the composition is able to withstand more or greater insults, exhibit greater protection from luminal antigens, or combinations thereof.

In some embodiments, the composition increases or enhances intestinal luminal integrity by increasing or improving one or more physiological parameters of luminal integrity. For example, increasing cGMP in the colon can protect the luminal surface by reducing reactivity and apoptosis of luminal epithelial cells in response to inflammatory stimuli, enhancing the mucus layer by promoting increased differentiation or numbers of goblet cells, increasing stimulation of mucus synthesis and/or secretion by goblet cells, or combinations thereof.

In some embodiments, a composition that increases the level of cGMP in the intestinal mucosa is administered in an effective amount to reduce cell death (i.e., apoptosis) at the luminal surface. In some embodiments, a composition that increases the level of cGMP in the intestinal mucosa is administered in an effective amount to reduce proliferation or hyperplasia in the crypt base.

In some embodiments, a composition that increases the level of cGMP in the intestinal mucosa protects the epithelial surface from damaging and inflammatory luminal contents by inducing downstream effectors of PKG mediated signaling. For example, in some embodiments, disclosed phosphodiesterase inhibitors are administered in an effective amount to maintain, increase, or activate DUSP8/10 (MKP5) expression. In another embodiment, the disclosed phosphodiesterase inhibitors are administered in an amount effective to maintain, increase, or activate FoxO3a expression, thereby increasing antioxidant capacity in the intestinal mucosa. In some embodiments, the disclosed phosphodiesterase inhibitor is administered in an effective amount to maintain, reduce, or decrease JNK activity levels.

It is believed that differentiation of intestinal cells, particularly differentiated secretory lineage cells, are important for maintaining the luminal barrier. Examples of differentiated secretory cells include, but are not limited to, goblet cells and enteroendocrine cells. Therefore, in some embodiments disclosed phosphodiesterase inhibitors are administered in an effective amount to increase the number of goblet cells or enteroendocrine cells. In some embodiments, the composition is administered in amount effective to increase differentiation of goblet cells or enteroendocrine cells.

1. Treatment of Diseases and Disorders Associated with Leaky Barrier

In some embodiments, correction of a leaky intestinal barrier can alleviate diseases associated with leaky intestinal barrier. Studies show that increased intestinal permeability plays a role in certain gastrointestinal conditions such as celiac disease, Crohn's disease, and irritable bowel syndrome. In one embodiment, the disclosed compounds can reverse leaky intestinal barrier and reduce the symptoms of celiac disease, Crohn's disease, or irritable bowel syndrome.

Recent studies show that leaky gut may be associated with other diseases such as lupus, type 1 diabetes, multiple sclerosis, chronic fatigue syndrome, fibromyalgia, arthritis, allergies, asthma, acne, autism, Parkinson's disease, eczema, psoriasis, chronic fatigue syndrome, multiorgan failure syndrome, non-alcoholic fatty liver disease, alcoholic cirrhosis, metabolic syndrome, rheumatoid arthritis, pancreatitis, obesity, and mental illness. In one embodiment, the disclosed compounds can reverse leaky intestinal barrier and reduce the symptoms of diseases such as lupus, type 1 diabetes, multiple sclerosis, chronic fatigue syndrome, fibromyalgia, arthritis, allergies, asthma, acne, autism, Parkinson's disease, eczema, psoriasis, chronic fatigue syndrome, multiorgan failure syndrome, non-alcoholic fatty liver disease, alcoholic cirrhosis, metabolic syndrome, rheumatoid arthritis, pancreatitis, obesity, and mental illness.

EXAMPLES

Example 1. General Synthesis of Compounds of Formula I

Scheme 1

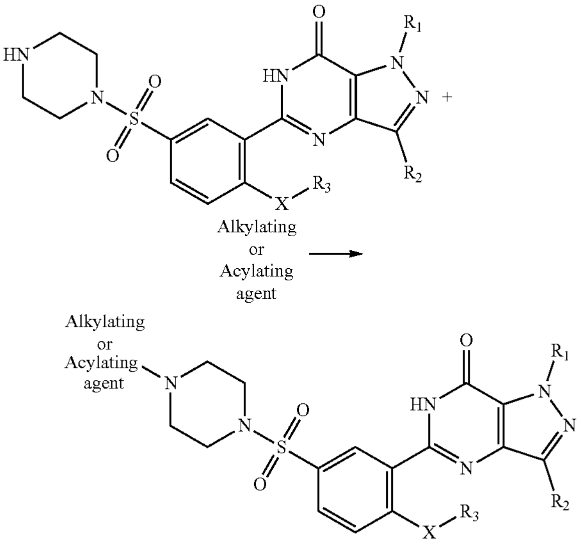

N-Desmethyl sildenafil or its structural NH— analog was dissolved in organic solvent followed by addition of an alkylating or acylating agent. The mixture was stirred at room temperature for 4-8 hours to isolate the product of Formula I as given in Scheme 1. If any of the starting materials contains a protecting group, a second step of deprotection was performed.

Example 2. General Synthesis of Compounds of Formula II

Scheme 2

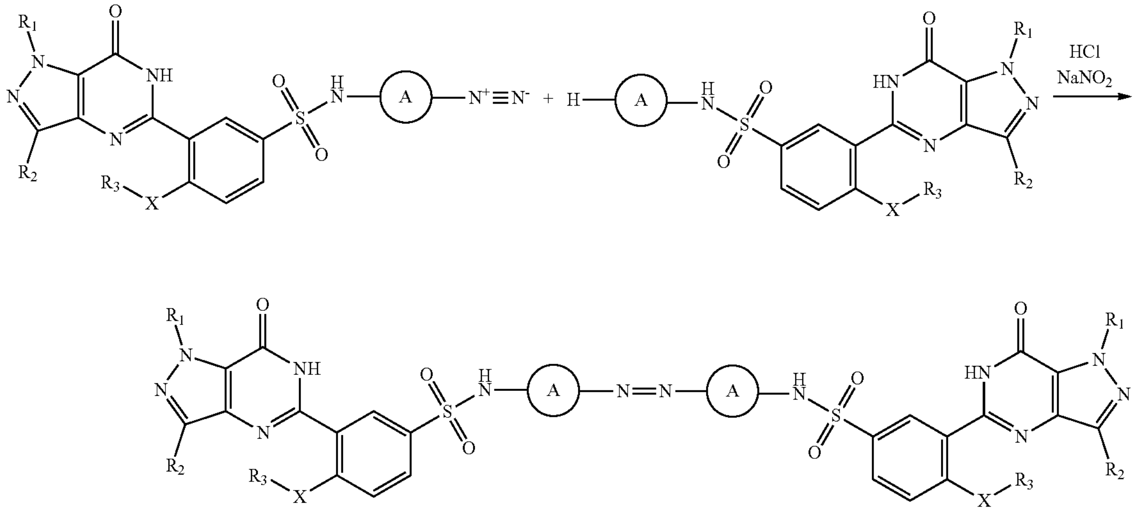

Prodrugs of Formula II were synthesized as a result of azo-coupling of the azo-containing building block and the one, which contained an acidic hydrogen under the acidic conditions. The diazotization was carried out using sodium nitrite and hydrochloric acid.

Example 3. General Synthesis of Compounds of Formula III

Scheme 3

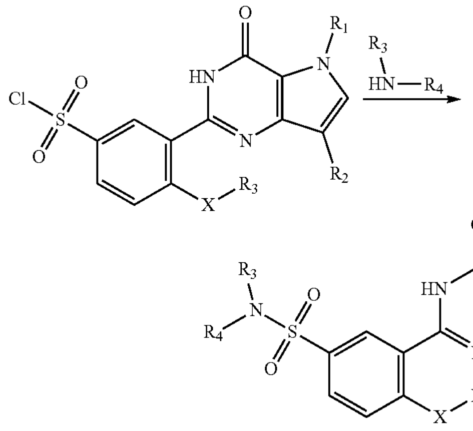

Synthesis of sulfonamides of formula III was carried out through the reaction of the halogen-containing reactive sulfonyl chloride and a moiety, which contains primary ($R_3$=H) or secondary amino group. Sulfonyl chloride was dissolved in an organic solvent followed by slow addition of equimolar amount of the amine in the presence of or tertiary organic base (e.g. triethylamine). Final product of Formula III is isolated after 4-8 hours of stirring the reaction mixture at room temperature. If any of the starting materials contains a protecting group, a second step of deprotection was performed to release all the reactive functional groups.

Example 4. The Effect of Carboxylic Acid Substitution for Methyl on Sildenafil's Permeability

Materials and Methods

Development of novel gut-targeted PDE5 inhibitors. Unique sildenafil analogs containing malonyl or boronyl groups were designed to be retained by the intestinal epithelium. Equal doses of sildenafil (Sil), malonyl-sildenafil (Mal), or boronyl-sildenafil (BOH) were given orally to mice and their entry into circulation after 1 hour was determined using LC-MS/MS of plasma specimens.

Permeability assay. Mice (n=6 per groups, 3 female and 3 male) were treated with either sildenafil or Mal by oral gavage at increasing doses. Plasma samples were obtained after 1 hour and subjected to analysis of sildenafil, desmethyl-sildenafil, or malonyl-sildenafil. Fecal pellets were collected between 2-4 hours following gavage and subjected to analysis of sildenafil, desmethyl-sildenafil, or malonyl-sildenafil.

Western blot and reporter cell lines. LS-174T colon cancer cells expressing PKG2 and PDE5 were treated with a low dose of linaclotide (Linzess) to measure PDE5 inhibitor activity. These reporter cells were treated with different doses of sildenafil (Sild) malonyl-sildenafil (Mal-Sild), boronyl-sildenafil (BOH), or an uncharged analog containing an acetyl group instead of malonate (CS-Mal) as indicated. Results shown are representative of at least 3 independent experiments.

Results

Unlike carboxylic acid substituents, uncharged structures such as boronic acid can also reduce systemic delivery by promoting transient covalent bonds that enhance retention in the gut lumen. The two lead compounds malonyl-sildenafil (Mal) and boronyl-sildenafil (BOH) that are analogs of the prototypical PDE5i sildenafil were synthesized. Also developed was an LC-MS/MS approach to measure both compounds in plasma and tissues.

Figure 2:
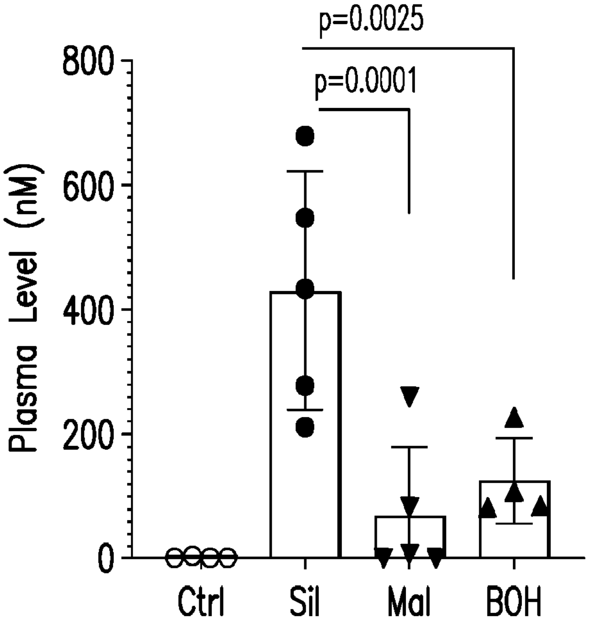
FIG. 2 is a bar graph showing plasma concentration of sildenafil and unique sildenafil analogs containing malonyl (Mal) or boronyl (BOH) groups. Data are means+/−SD, analysis used one-way ANOVA with Tukey's post hoc test.
Figure 3A:
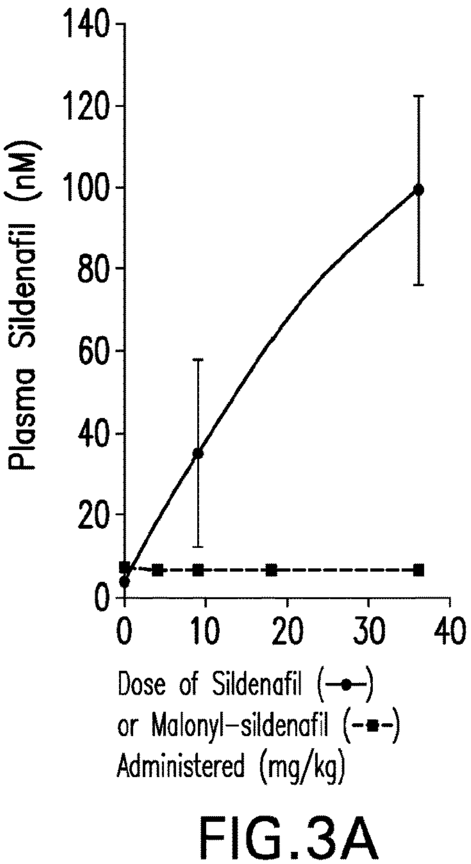
FIGS. 3A-3C are line graphs showing plasma concentration of sildenafil (FIG. 3A), desmethyl-sildenafil (FIG. 3B) and malonyl-sildenfil (FIG. 3C) in mice treated with sildenafil (black line) or malonyl-sildenafil (dashed line).
Figure 3B:
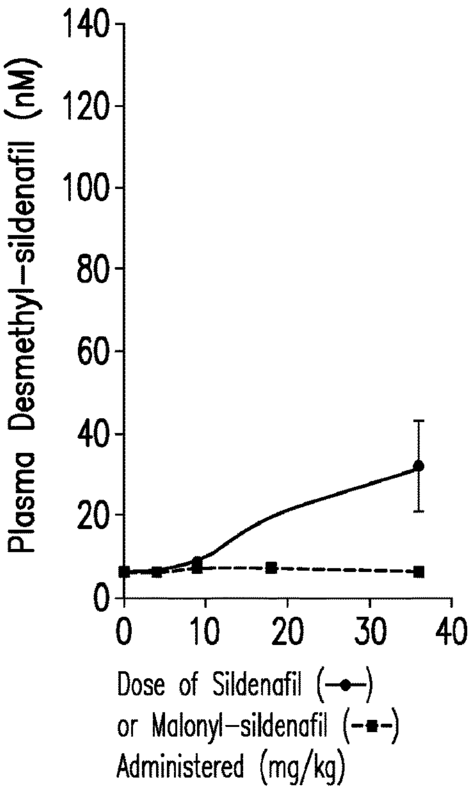
Figure 3C:
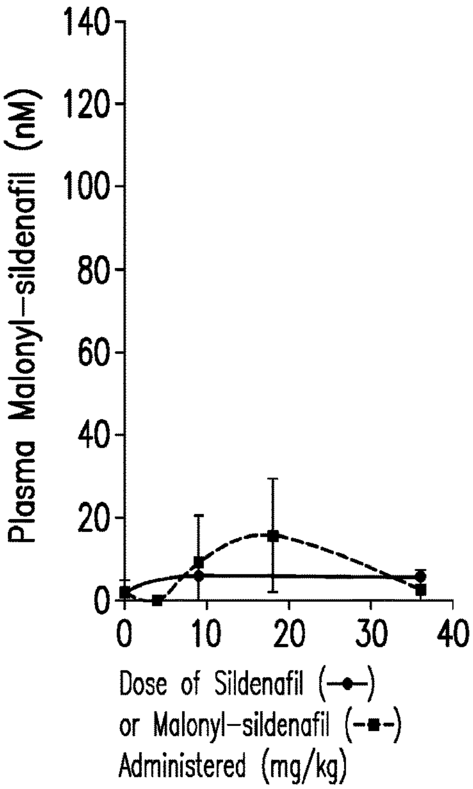
Figure 3D:
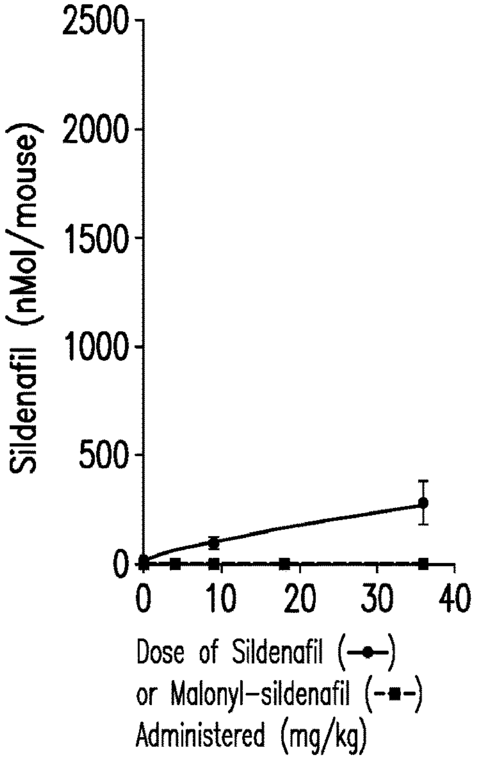
FIGS. 3D-3F are line graphs showing fecal concentration of sildenafil (FIG. 3D), desmethyl-sildenafil (FIG. 3E), and malonyl-sildenafil (FIG. 3F) in mice treated with sildenafil (black line) or malonyl-sildenafil (dashed line).
Figure 3E:
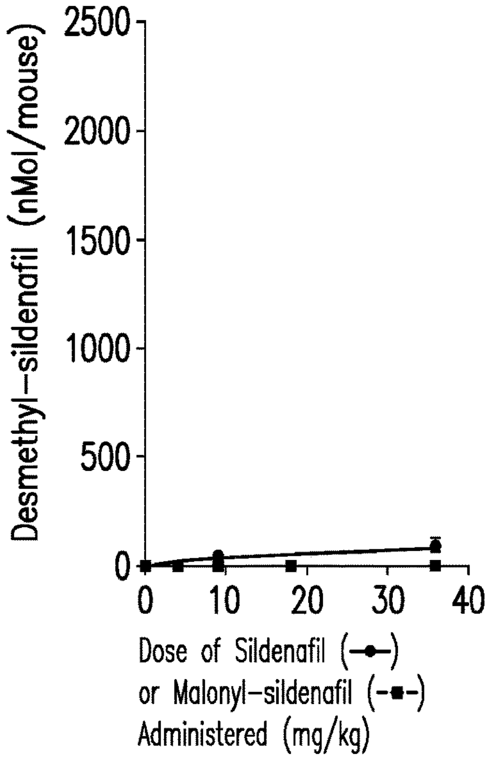
Figure 3F:
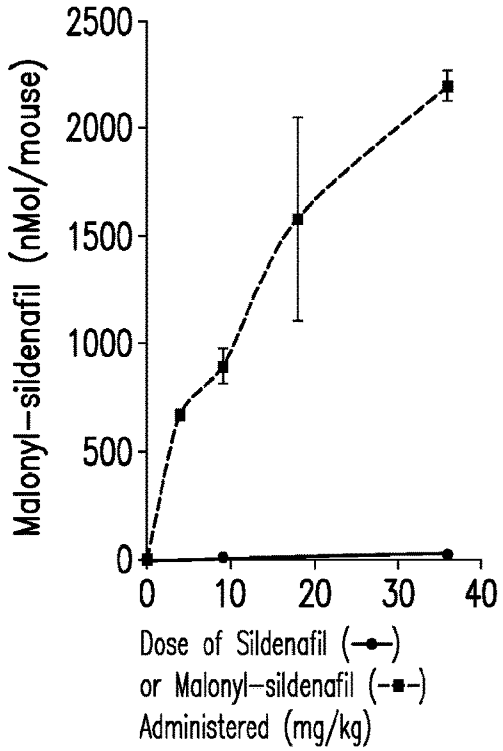

Both compounds exhibit minimal entry into plasma of mice compared to the parent compound following oral administration at 5.7 mg/kg, which is 4 times the human dose, or ⅓rd the equivalent mouse dose (FIG. 2). Sildenafil was not detected in control mice (Ctrl) that were not given drug.

Because the central tenant of the disclosed compositions is that the modifications reduce permeability of the compositions across the epithelial and endothelial membrane barriers to enter the circulation, it was important to demonstrate that high-doses were still gut-retained. A full dose curve using orally administered Mal from 4 mg/kg up to 36 mg/kg demonstrated minimal entry from the gut into the plasma of mice (FIGS. 3A-3F). Desmethyl-sildenafil is an active phase 1 metabolite of sildenafil that could be a hydrolytic cleavage product of Mal suggesting a possible pro-drug for desmethyl-sildenafil. It was therefore important to demonstrate that Mal was not "missed" by the LC-MS/MS protocol due to chemical modification in vivo. At high doses of sildenafil administration, desmethyl-sildenafil was detected in both plasma and feces of mice treated with sildenafil but not in mice treated with Mal. While Mal was not found to increase in the plasma of mice following oral administration of increasing doses, it was largely recovered in the feces a few hours following gavage in a dose-dependent manner. This contrasted with sildenafil and desmethyl-sildenafil that increased dramatically in the plasma, but only small quantities were detected in the feces during the time period studied.

Figure 4A:
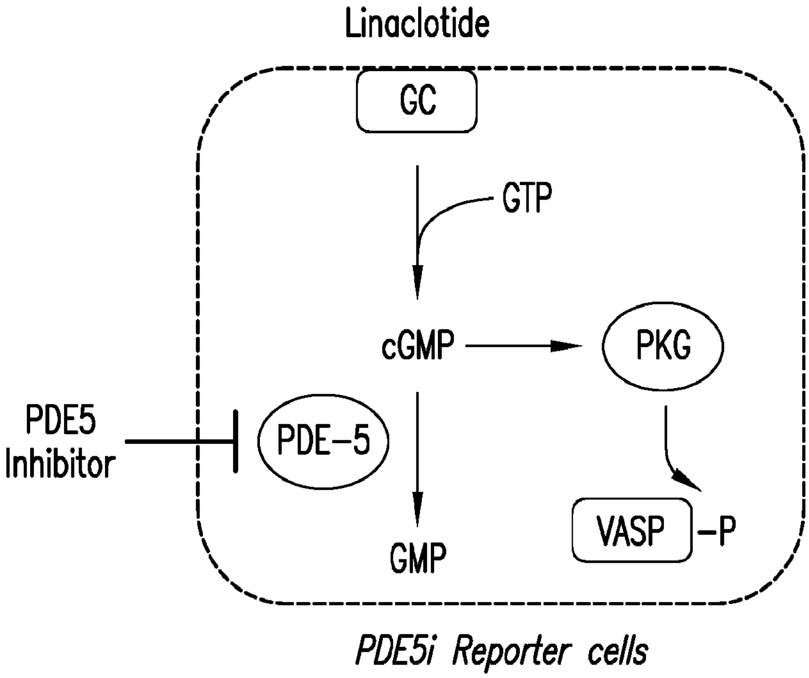
FIG. 4A is a diagram describing the reporter cell assay in which LS-174T colon cancer cells expressing PKG2 and PDE5 are treated with a low dose of linaclotide to measure PDE5i activity.
Figure 4B:
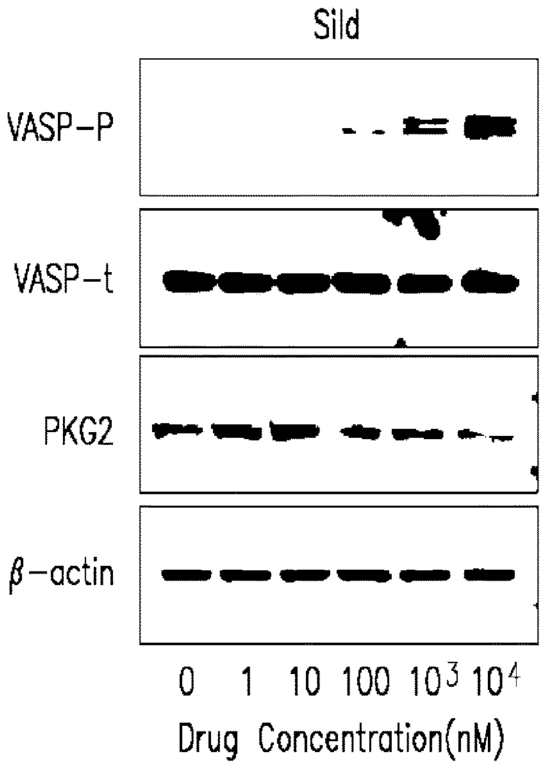
FIGS. 4B-4E are Western blots showing expression of phospho-VASP, total VASP, PKG2 and β-actin in reporter cells were treated with different doses of sildenafil (Sild) (FIG. 4B), malonyl-sildenafil (Mal-Sild) (FIG. 4C), boronyl-sildenafil (BOH) (FIG. 4D), or an uncharged analog containing an acetyl group instead of malonate (CS-Mal) (FIG. 4E). Results shown are representative of at least 3 independent experiments.
Figure 4C:
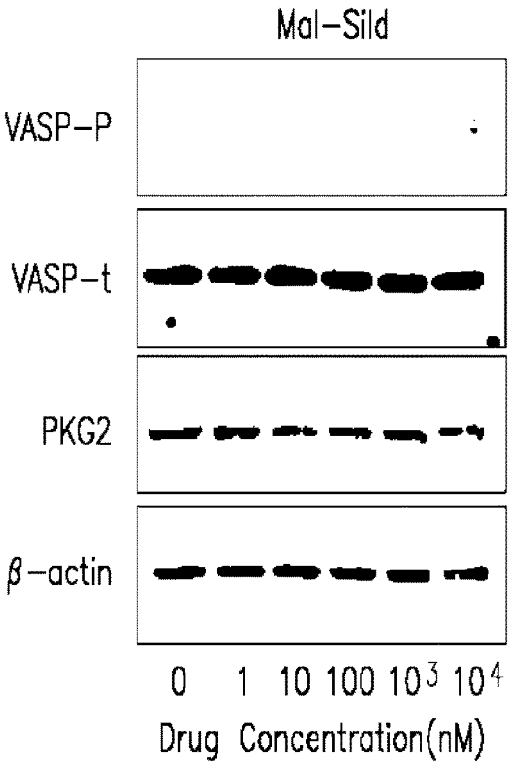
Figure 4D:
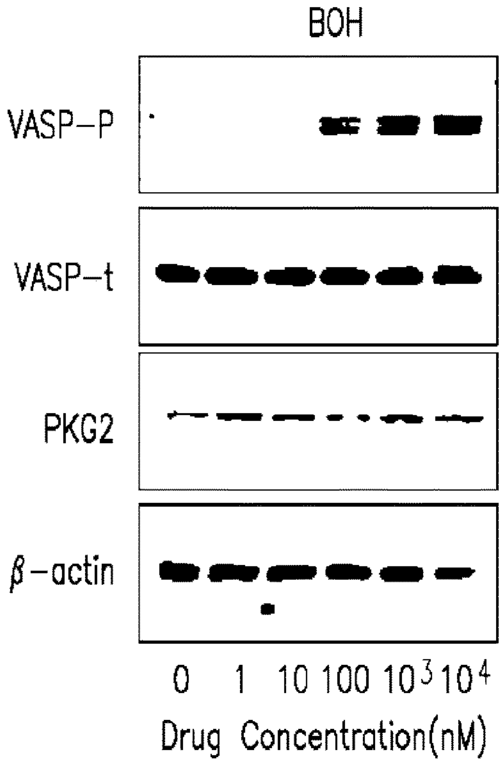
Figure 4E:
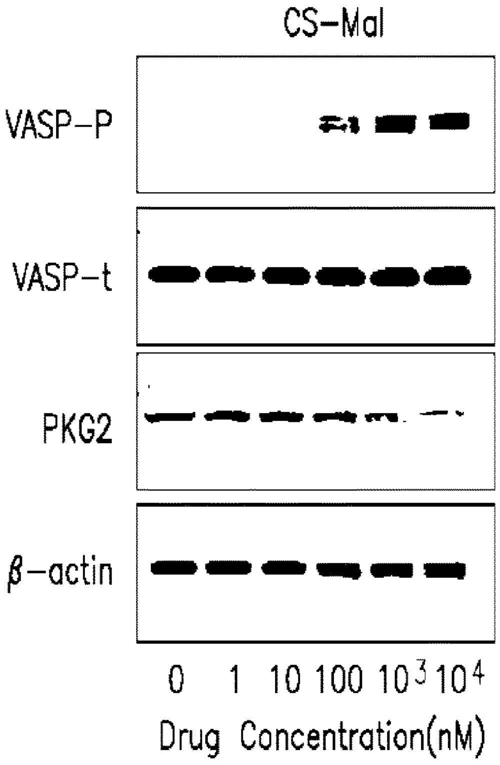

Proof of principle for gut-retention of Mal relative to the parent compound sildenafil was demonstrated, so evidence demonstrating that the sildenafil analogs can enter colon epithelial cells and inhibit the activity of the PDE5 target enzyme was a next step. This was demonstrated for several analogs using a novel reporter cell line in which biologically relevant PDE5 inhibitor activity (e.g. cGMP levels sufficient to activate downstream signaling) is indirectly measured by detecting phosphorylation of the PKG2 substrate vasodilator-stimulated phosphoprotein (VASP) (FIG. 4A). In this system all analogs retained PDE5 inhibitor activity, but Mal was 1/100 as potent as sildenafil and BOH (FIGS. 4B-4E). This was most likely due to reduced cell entry due to the carboxylic acid group because an acetyl-sildenafil was equally potent as the parent compound.

Example 5. Pharmacodynamic Evidence

Materials and Methods

Toxicity studies and histology. Mice were treated with either normal drinking water (Ctrl), or drinking water containing the drugs Sildenafil (Sild), Malonyl-sildenafil (Mal), or Boronyl-sildenafil (BOH) for 8 days. The body weight was measured daily. After 8 days the animals were sacrificed and the epithelial proliferation in the colon was measured by flow cytometry using Ki67. Box plots show median and whiskers are min and max values. The p values were generated using a one-way ANOVA with Dunnett's multiple comparisons test. For FIGS. 5A and 5C, n=5.

Intestinal transit studies. Mice (n=6) were subjected to opioid induced constipation by treating with loperamide (10 mg/kg) or loperamide containing malonyl-sildenafil (Lop+Mal). The transit time was measured by gavage of a charcoal meal one hour later and measuring time until the black fecal pellet was expelled (left panel).

Barrier assay. Mice (n=10) were treated with 2% Dextran sulfate sodium in the drinking water for 5 days followed by gavage with FITC-dextran (100 μL of 100 mg/ml) and then measurement of FITC fluorescence in plasma after 2 hr. Box plots show median and whiskers are min and max values. The p values were generated using a one-way ANOVA with Dunnett's multiple comparisons test.

Results

Figure 5A:
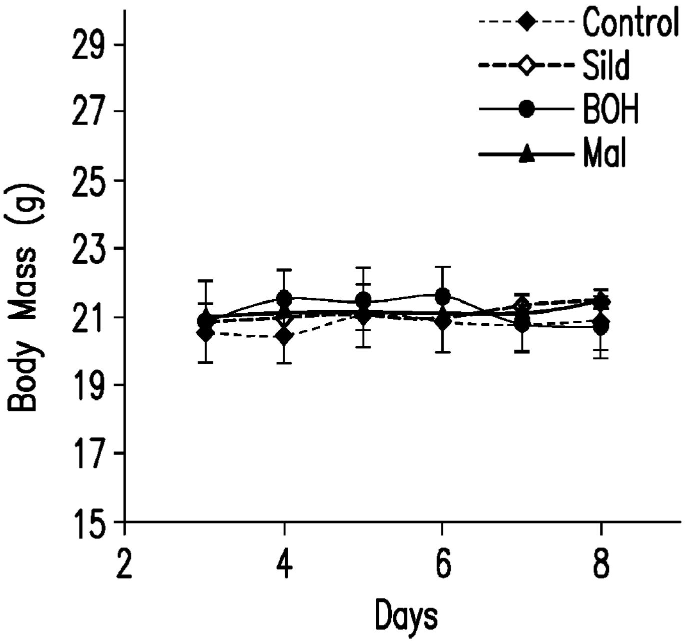
FIG. 5A is a line graph showing body weight over time for control mice (Ctrl) or mice treated with either Sildenafil (Sild), Malonyl-sildenafil (Mal), or Boronyl-sildenafil (BOH) in the drinking water for 8 days. After 8 days the animals were sacrificed and the epithelial proliferation in the colon was measured by flow cytometry using Ki67 (FIG. 4B and FIG. 4C). Box plots show median and whiskers are min and max values. The p values were generated using a one-way ANOVA with Dunnett's multiple comparisons test. For both B and C, n=5.
Figure 5B:
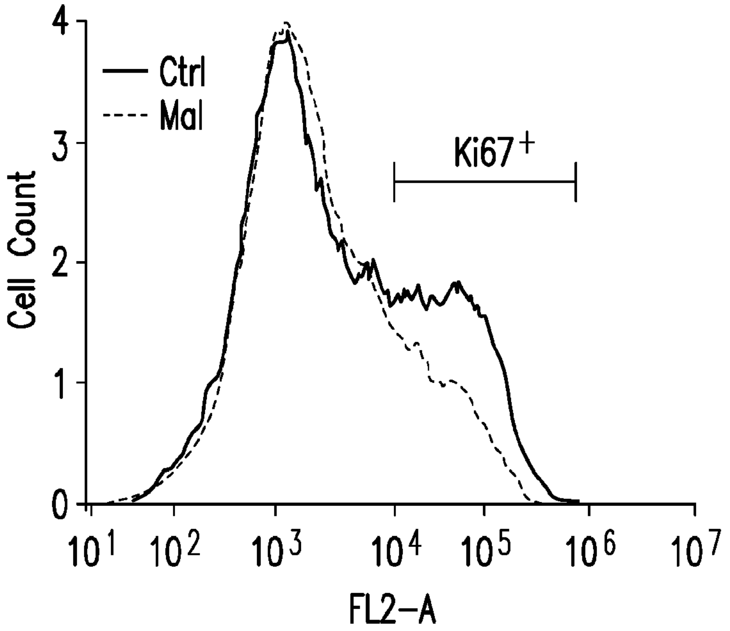
Figure 5C:
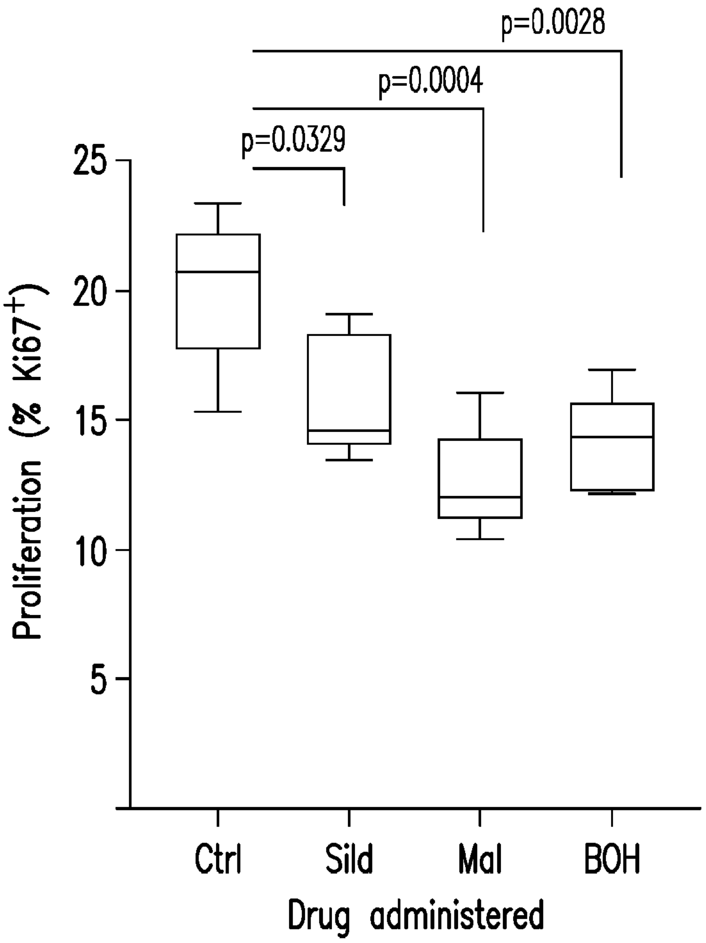

Most important to the therapeutic claims for the non-systemic sildenafil analogs is that they are able to affect the gut in a manner that has been published for conventional PDE5 inhibitors. Preliminary results demonstrated that neither Mal or BOH were toxic to animals when administered at a daily dose of 5.7 mg/kg in the drinking water over an 8-day period based upon body weight (FIG. 5A). Importantly, both Mal and BOH treatment significantly reduced total proliferation in the colon epithelium (FIG. 5C). Mal reduced total Ki67 positive cells almost by half, from 21% to 12%, which exceeded the effect of sildenafil (15%).

Figure 6A:
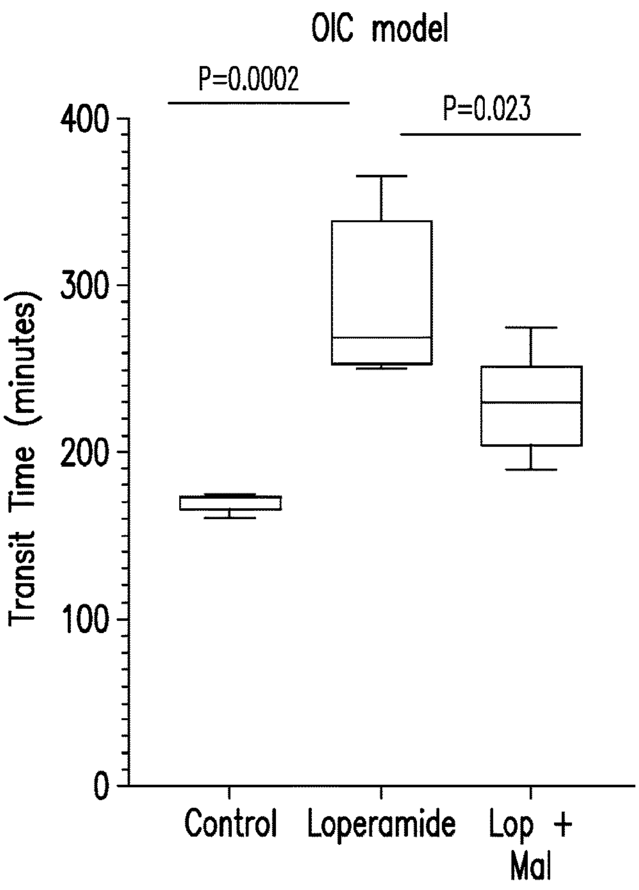
FIG. 6A is a box and whisker plot showing intestinal transit time (minutes) in control mice and mice treated with loperamide or loperamide plus malonyl-sildenafil (Lope+mal).

Suppression of proliferation in the colon epithelium is a surrogate marker for colon cancer prevention since this effect is part of the mechanism. Additional evidence for the therapeutic effects of Mal that have previously been published for sildenafil is the ability to normalize transit in an opioid induced constipation model (FIG. 6A).

Figure 6B:
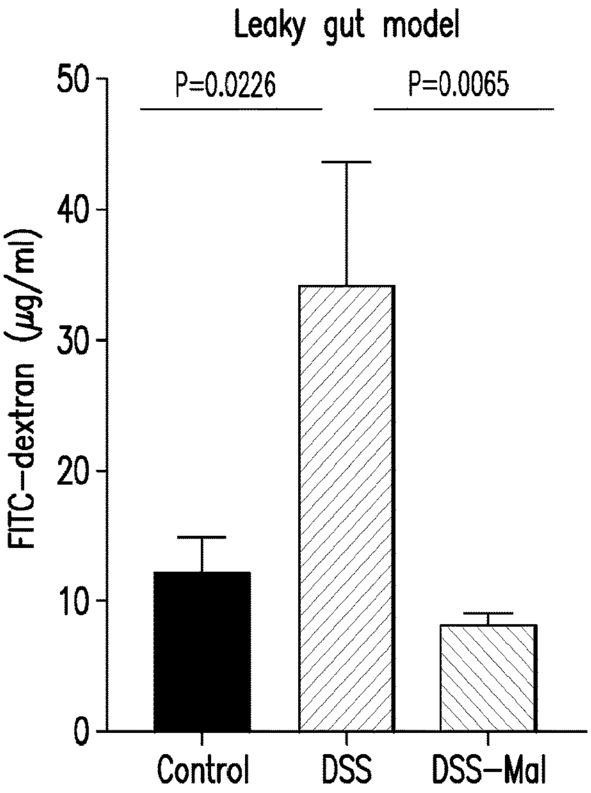
FIG. 6B is a bar graph showing FITC dextran concentration in plasma of control mice, and mice treated with DSS alone, or DSS plus malonyl-sildenafil (DSS-mal).

Intestinal barrier permeability has been associated with a plethora of intestinal diseases and may underlay other extra-intestinal pathologies that are currently under investigation. The cGMP signaling pathway is important to the maintenance of the intestinal barrier, which can be strengthened by PDE5 inhibitor treatment. In a post-infectious IBS model that has barrier dysfunction, Mal treatment dramatically increased barrier function by the same level as previously published for sildenafil in this model (FIG. 6B).

While in the foregoing specification this invention has been described in relation to certain embodiments thereof, and many details have been put forth for the purpose of illustration, it will be apparent to those skilled in the art that the invention is susceptible to additional embodiments and that certain of the details described herein can be varied considerably without departing from the basic principles of the invention.

All references cited herein are incorporated by reference in their entirety. The present invention may be embodied in other specific forms without departing from the spirit or essential attributes thereof and, accordingly, reference should be made to the appended claims, rather than to the foregoing specification, as indicating the scope of the invention.

We claim:

1. A compound of Formula I:

Formula I

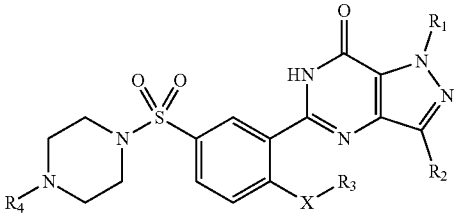

or a pharmaceutically acceptable salt, solvate, stereoisomer, or tautomer thereof, wherein:

$R_1$ is $C_{1-10}$ alkyl, wherein the $C_{1-10}$ alkyl is optionally substituted with one or more substituents independently selected from the group consisting of halogen, CN, $NO_2$, $B(OH)_2$, C(O)H, $C(O)CH_3$, $C(O)NH_2$, C(O)OH, $NH_2$, OH, $OC_{1-10}$ alkyl, $S(O)_2NH_2$, $S(O)_2OH$, $S(O)_2ONa$, $C_{3-10}$ cycloalkyl, aryl, and heteroaryl;

$R_2$ is $C_{1-10}$ alkyl, wherein the $C_{1-10}$ alkyl is optionally substituted with one or more substituents independently selected from the group consisting of halogen, CN, $NO_2$, $B(OH)_2$, C(O)H, $C(O)CH_3$, $C(O)NH_2$, C(O)OH, $NH_2$, OH, $OC_{1-10}$ alkyl, $S(O)_2NH_2$, $S(O)_2OH$, $S(O)_2ONa$, $C_{3-10}$ cycloalkyl, aryl, and heteroaryl;

X is —O—;

$R_3$ is $C_{1-10}$ alkyl, $OC_{1-10}$ alkyl, $C_{3-10}$ cycloalkyl, aryl, or heteroaryl, wherein the $C_{1-10}$ alkyl is substituted with one or more substituents independently selected from the group consisting of halogen, CN, $NO_2$, $B(OH)_2$, C(O)H, $C(O)CH_3$, $C(O)NH_2$, C(O)OH, $NH_2$, OH, $OC_{1-10}$ alkyl, $S(O)_2NH_2$, $S(O)_2OH$, $S(O)_2ONa$, $C_{3-10}$ cycloalkyl, aryl, and heteroaryl;

$R_4$ is $C(O)R_8$, $C(O)CH_2C(O)OH$, $C(O)(CH_2)_nNR_6R_7$, $C(O)CH(R_9)NH_2$, $C(O)CH(R_9)OH$, or $C(O)C(O)R_{10}$;

$R_6$ is H or $C_{1-10}$ alkyl;

$R_7$ is H or $C_{1-10}$ alkyl;

$R_8$ is $C_{1-10}$ alkyl;

$R_9$ is $C_{1-10}$ alkyl;

$R_{10}$ is $C_{1-10}$ alkyl; and n is 1, 2, 3, 4, 5, or 6.

2. The compound of claim 1, or a pharmaceutically acceptable salt, solvate, stereoisomer, or tautomer thereof, wherein $R_4$ is $C(O)CH_2CH_2CH_3$, $C(O)CH_2NH_2$, $C(O)CH_2N(CH_3)_2$, $C(O)CH_2CH_2N(CH_3)_2$, $C(O)CH(CH_3)NH_2$, $C(O)CH(CH_3)OH$, or $C(O)C(O)CH_3$.

3. The compound of claim 1, or a pharmaceutically acceptable salt, solvate, stereoisomer, or tautomer thereof, wherein $R_4$ is $C(O)CH_2C(O)OH$.

4. A compound of Formula I:

Formula I

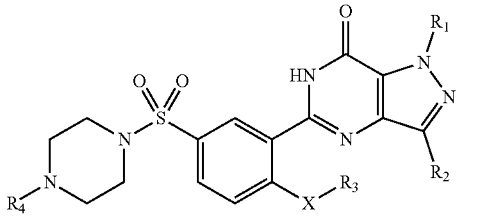

or a pharmaceutically acceptable salt, solvate, stereoisomer, or tautomer thereof, wherein:

$R_1$ is $C_{1-10}$ alkyl;

$R_2$ is $C_{1-10}$ alkyl;

X is —O—;

$R_3$ is $C_{1-10}$ alkyl;

$R_4$ is $C(O)R_8$, $C(O)CH_2C(O)OH$, $C(O)(CH_2)_nNR_6R_7$, $C(O)CH(R_9)NH_2$, $C(O)CH(R_9)OH$, or $C(O)C(O)R_{10}$;

$R_6$ is H or $C_{1-10}$ alkyl;

$R_7$ is H or $C_{1-10}$ alkyl;

$R_8$ is $C_{1-10}$ alkyl;

$R_9$ is $C_{1-10}$ alkyl;

$R_{10}$ is $C_{1-10}$ alkyl; and n is 1, 2, 3, 4, 5, or 6.

5. The compound of claim 4, or a pharmaceutically acceptable salt, solvate, stereoisomer, or tautomer thereof, wherein $R_4$ is $C(O)CH_2CH_2CH_3$, $C(O)CH_2NH_2$, $C(O)CH_2N(CH_3)_2$, $C(O)CH_2CH_2N(CH_3)_2$, $C(O)CH(CH_3)NH_2$, $C(O)CH(CH_3)OH$, or $C(O)C(O)CH_3$.

6. The compound of claim 4, or a pharmaceutically acceptable salt, solvate, stereoisomer, or tautomer thereof, wherein $R_4$ is $C(O)CH_2C(O)OH$.

7. The compound of claim 4, wherein the compound is:

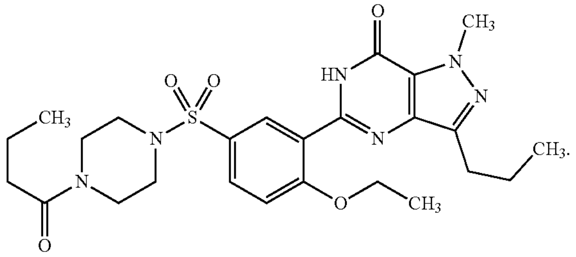 [SMILES: CCCC(=O)N1CCN(S(=O)(=O)c2ccc(OCC)c(-c3nc4c(CCC)nn(C)c4c(=O)[nH]3)c2)CC1]

8. The compound of claim 4, or a stereoisomer thereof, wherein the compound, or stereoisomer thereof, is selected from the group consisting of:

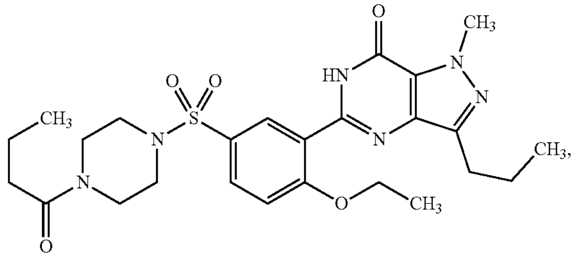

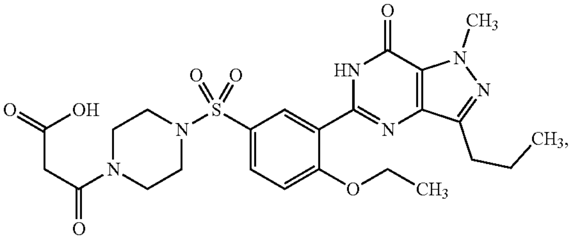

-continued

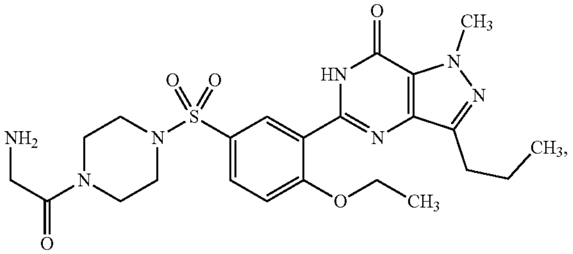

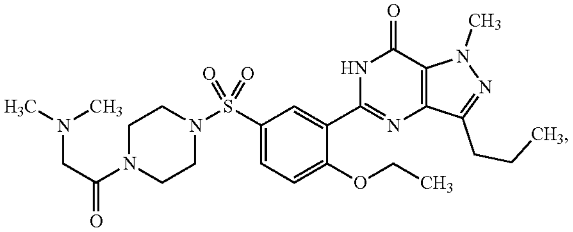

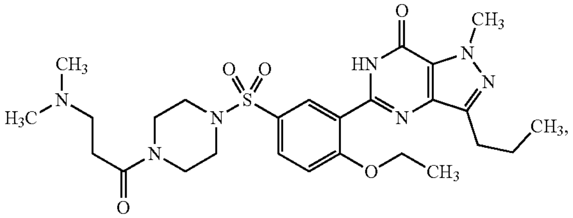

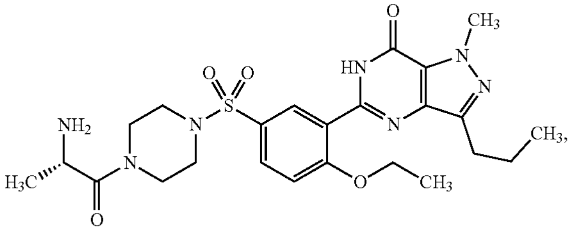

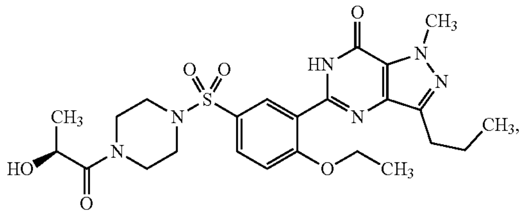

and

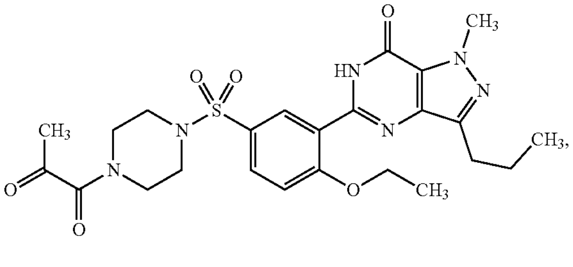

or a pharmaceutically acceptable salt, solvate, or tautomer thereof.

* * * * *